(12) United States Patent
Lee et al.

(10) Patent No.: US 10,568,513 B2
(45) Date of Patent: Feb. 25, 2020

(54) MULTIPLE IMPLANT COMMUNICATIONS WITH ADJUSTABLE LOAD MODULATION USING MODULATION INDICES

(71) Applicant: The Alfred E. Mann Foundation for Scientific Research, Valencia, CA (US)

(72) Inventors: Edward K. F. Lee, Fullerton, CA (US); Harshit R. Suri, Pasadena, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 0 days.

(21) Appl. No.: 15/907,457

(22) Filed: Feb. 28, 2018

(65) Prior Publication Data

US 2018/0256030 A1    Sep. 13, 2018

Related U.S. Application Data

(60) Provisional application No. 62/468,226, filed on Mar. 7, 2017.

(51) Int. Cl.
*A61B 5/00* (2006.01)
*H04Q 9/00* (2006.01)
*H04B 17/318* (2015.01)
*A61F 2/72* (2006.01)
(Continued)

(52) U.S. Cl.
CPC ........ *A61B 5/0031* (2013.01); *A61B 5/04888* (2013.01); *A61F 2/583* (2013.01);
(Continued)

(58) Field of Classification Search
CPC .............. A61B 5/0031; A61B 5/04888; A61B 2560/0219; A61F 2/583; A61F 2/72;
(Continued)

(56) References Cited

U.S. PATENT DOCUMENTS 5,314,457 A * 5/1994 Jeutter .................. A61N 1/372
                                                        128/903
5,476,488 A   12/1995 Morgan et al.
(Continued)

FOREIGN PATENT DOCUMENTS

WO    WO2015139053    9/2015

OTHER PUBLICATIONS

Implantable Myoelectric Sensors (IMESs) for Intramuscular Electromyogram Recording, IEEE Transactions on Biomedical Engineering, vol. 56, No. 1, Jan. 2009, pp. 159-171.
(Continued)

*Primary Examiner* — Amine Benlagsir
(74) *Attorney, Agent, or Firm* — Michael J. Bolan; Vista IP Law Group, LLP

(57) ABSTRACT

A medical system and method of communicating between a telemetry controller and a plurality of medical devices implanted within a patient is provided. Communication links are respectively established between the telemetry controller and the implanted medical devices. The communication links are respectively amplitude modulated by the implanted medical devices at modulation levels using load modulation. Received signal strength indicators (RSSIs) of the amplitude modulated communication links for the implanted medical devices are measured. A variation of the RSSIs is decreased by modifying, based on the measured RSSIs, at least one modulation level at which the respective at least one communication link is amplitude modulated by the respective implanted medical device(s).

46 Claims, 15 Drawing Sheets

(51) Int. Cl.
*A61B 5/0488* (2006.01)
*A61F 2/58* (2006.01)
*A61F 2/70* (2006.01)

(52) U.S. Cl.
CPC ............ *A61F 2/72* (2013.01); *H04B 17/318* (2015.01); *H04Q 9/00* (2013.01); *A61B 2560/0219* (2013.01); *A61F 2002/705* (2013.01); *H04Q 2209/40* (2013.01); *H04Q 2209/88* (2013.01)

(58) Field of Classification Search
CPC .. A61F 2002/705; H04B 17/318; H04Q 9/00; H04Q 2209/40; H04Q 2209/88
See application file for complete search history.

(56) References Cited

U.S. PATENT DOCUMENTS

| | | |
|---|---|---|
| 2007/0260293 A1 | 11/2007 | Carpenter et al. |
| 2008/0140154 A1 | 6/2008 | Loeb et al. |
| 2010/0198304 A1* | 8/2010 | Wang ................... A61N 1/3727 607/60 |
| 2012/0109258 A1* | 5/2012 | Cinbis ................. A61B 5/0028 607/60 |
| 2012/0294386 A1* | 11/2012 | Ghovanloo .......... A61N 1/3727 375/295 |
| 2016/0302686 A1 | 10/2016 | Einarsson et al. |
| 2017/0257761 A1 | 9/2017 | Rodriguez et al. |

OTHER PUBLICATIONS

PCT International Search Report for PCT/US2018/020140, Applicant: The Alfred E. Mann Foundation for Scientific Research, Form PCT/ISA/210 and 220, dated Jun. 11, 2018 (7pages).

PCT Written Opinion of the International Search Authority for PCT/US2018/020140, Applicant: The Alfred E. Mann Foundation for Scientific Research, Form PCT/ISA/237, dated Jun. 11, 2018 (4pages).

* cited by examiner

MULTIPLE IMPLANT COMMUNICATIONS WITH ADJUSTABLE LOAD MODULATION USING MODULATION INDICES

CLAIM OF PRIORITY

Pursuant to 35 U.S.C. § 119(e), this application claims the benefit of U.S. Provisional Patent Application 62/468,226, filed Mar. 7, 2017, which is expressly incorporated herein by reference.

FIELD OF THE INVENTION

The present invention generally relates to wireless power/data transfer techniques in medical systems, and specifically relates to such techniques for use in wirelessly providing power to and receiving uplink data from multiple implantable devices.

BACKGROUND OF THE INVENTION

In the field of wireless power and data transfer, inductive coupling has been used to provide power to and communicate with a device without making electrical contact. This technique has been used, for example, with implanted medical systems. For implantable systems, multiple medical devices can be implanted inside of the body of a patient. Medical systems utilizing this technique have an external control unit, such as a telemetry controller (TC), and one or more medical devices implanted within the body of a patient. Power transfer and data communication between the external control unit and implanted medical device(s) are provided via an inductive link.

For example, as illustrated in FIG. 1, a conventional power/data transfer system 10 typically includes an external TC 12 capable of performing a medical function (which could be diagnostic and/or therapeutic) and a plurality of implantable medical devices ("implants") 14, (only two implants 14(y), 14(z) are shown for purposes of brevity in illustration), each of which is capable of sensing physiological signals in the body of a patient and transmitting representative data to the TC 12 in furtherance of performing the medical function.

A primary coil Lp located inside the TC 12 inductively couples and powers secondary coils Ls(y), Ls(z) respectively inside the implanted medical devices 14(y), 14(z). Power is delivered to the implanted medical devices 14 by applying an alternating current (AC) current on the primary coil Lp at a selected transmission frequency Ft. Capacitors Cs(y), Cs(z) are respectively coupled in parallel to the secondary coils Ls(y), Ls(z) to form LC tank circuits that are tuned to resonant at the transmission frequency Ft. In addition to providing power to the medical devices, the coils Lp's and Ls's are also utilized for communication between the TC 12 and the implanted medical devices 14. For downlink data from the TC 12 to the implanted medical devices 14, different modulation techniques can be applied to the AC current on the primary coil Lp.

For uplink data from the implanted medical devices 14 to the TC 12, a load modulation technique can be used. In this technique, each implanted medical device 14 transmits uplink data to the TC 12 in a given time slot in a time-division multiplexed manner by modulating a load resistance Rs to a modified load resistance Rs+ΔRs according to the uplink data, where $\Delta R_L$ is the amount of change on the load resistance. Due to the inductive coupling between the primary coil Lp and the corresponding secondary coil Ls, a voltage amplitude change on the primary coil Lp according to the uplink data is obtained. Based on the amplitude change, the TC 12 can demodulate the data sent from a particular implanted medical device 14 at the corresponding time slot utilizing any one or more of a variety of demodulation techniques, including amplitude shift keying (ASK), phase shift keying (PSK), frequency shift keying (FSK), etc.

The amplitudes of the signals received by the TC 12 from the implanted medical devices 14 may different from each other. For example, depending on the distances, as well as the characteristic of the material, between the primary coil Lp and the secondary coils Ls(y), Ls(z), the coupling coefficients Kc(y), Kc(z) between the primary coil Lp and the respective secondary coils Ls(y), Ls(z) can be different for the different implanted medical devices 14(y), 14(z). The difference in the respective coupling coefficients Kc(y), Kc(z) between the primary coil Lp and the secondary coils Ls(y), Ls(z) will affect the voltage amplitudes on different secondary coils Ls(y), Ls(z). Furthermore, if each medical device 14 utilizes the same amount of load resistance change ΔRs for load modulating the uplink data, the voltage amplitude induced on the primary coil Lp for each implanted medical device 14 will also be different. These voltage amplitude differences on the primary coil Lp due to different coupling coefficients Kc(y), Kc(z) will complicate the circuitry inside the TC 12 that demodulates the uplink data from the induced voltage on the primary coil Lp. Thus, the received signal amplitudes corresponding to the respective implanted medical devices 14(y), 14(z) may be primarily affected by the coupling coefficients Kc(y), Kc(z). The received signal amplitudes corresponding to the respective implanted medical devices 14(y), 14(z) may also be secondarily affected by the different tuning tolerances between the primary coil Lp and the respective secondary coils Ls(y), Ls(z).

For example, referring to FIG. 2, the changes in the amplitude of AC voltage induced on the primary coil Lp due to load modulations at the secondary coils Ls are represented as changes in an envelope signal Senv. A simple demodulator design utilizes an envelope detector to extract the envelope signal Senv from the amplitude changes induced on the primary coil Lp, and a comparator to compare the envelope signal Senv with an appropriate threshold level Sth to determine the uplink data. In the embodiment illustrated in FIG. 2, an ASK modulation technique is employed to encode the envelope signal Senv with data that can then be demodulated to acquire the data therefrom.

For example, as shown in FIG. 3a, an ASK modulated envelope signal Senv1, which contains one of two bits of information ("1" or "0") during each symbol period (indicated between the dashed lines), can be converted into a digital signal by comparing the envelope signal Senv1 to a threshold level Sth. The data value can be read as switching between "0" and "1" if and when the envelope signal Senv1 crosses the threshold level Sth in the respective symbol period, i.e., from "0" to "1" when the envelope signal Senv1 rises above the threshold level Sth, and from "1" to "0" when the envelope signal Senv1 falls below the threshold level Sth.

In an alternative embodiment shown in FIG. 3b, a four-phase (0°, 90°, 180°, and) 270° PSK modulated envelope signal Senv2, which contains two bits of information ("00," "01," "10," and "11") during each symbol period (indicated between the dashed lines), can be converted into a digital signal by comparing the envelope signal Senv2 to a threshold level Sth. The data value can be read as being "00," "01,"

"10," and "11," depending on when and in what direction the envelope signal Senv2 crosses the threshold level Sth in the respective symbol period.

In still another alternative embodiment shown in FIG. 3c, an FSK modulated envelope signal Senv3, which contains one of two bits of information ("1" or "0") during each symbol period (indicated between the dashed lines), can be converted into a digital signal by comparing the envelope signal Senv3 to a threshold level Sth. The data value can be read as "0" and "1," depending on how many times the envelope signal Senv3 crosses the threshold level Sth in the respective symbol period, i.e., a "0" if the envelope signal Senv crosses the threshold level Sth three or less times (resulting from the relatively low-frequency portion of the envelope signal Senv), a "1" if the envelope signal Senv cross the threshold level Sth more than three times (resulting from the relatively high-frequency portion of the envelope signal Senv3)

Regardless of the type of demodulation technique, when the coupling coefficients Kc between the primary coil Lp and the secondary coils Ls(y), Ls(z) of the implanted medical devices $14(y)$, $14(z)$ differ, the peak-to-peak amplitudes of the envelope signals Senv on the primary coil Lp for the implanted medical devices $14(y)$, $14(z)$ will be different. In this case, the peak-to-peak amplitude of the envelope signal Senv for the implanted medical device $14(y)$ with a relatively high coupling coefficient Kc(y) will be greater than the peak-to-peak amplitude of the envelope signal Senv for the implanted medical device $14(z)$ with a relatively low coupling coefficient Kc(z). Thus, different threshold level values St(y), St(z) are respectively required to correctly demodulate the uplink data for the implanted medical devices $14(y)$, $14(z)$.

Because a single threshold level value St cannot be used to demodulate the uplink data from the different implanted medical devices 14, a more complicated demodulator design utilizing equalization techniques for the envelope signals Senv is required. If the coupling coefficients Kc drift in time, an even more complicated demodulator design using adaptive equalization will become necessary. Alternatively, AC coupling can be used between the envelope detector and the comparator, such that the average value of the envelope signal Senv for the uplink data sent by the different implanted medical devices 14 will move to ground, and thus, the threshold level St can be set to ground. The uplink data can therefore be correctly demodulated from the envelope signal Senv. However, because it will take some time to have the average value of the envelope signal Senv to move to ground at the output of the AC coupling whenever a different implanted medical device sends out uplink data, the data within the time required for settling the average value of the envelope signal Senv to ground cannot be reliably detected without significantly reducing the uplink data transmission rate.

There, thus, remains a need for providing a simpler means that allows demodulation of uplink data sent from multiple implantable medical devices without having to reduce the uplink data transmission rate.

SUMMARY OF THE INVENTION

In accordance with a first aspect of the present inventions, a medical system comprises a plurality of implantable medical devices, and a telemetry controller (e.g., an external telemetry controller) configured for establishing communication links between the implantable medical devices and the telemetry controller. The implantable medical devices are configured for amplitude modulating the communication links at modulation levels, and the telemetry controller is further configured for respectively measuring received signal strength indicators (RSSIs) of the amplitude modulated communication links, and decreasing a variation of the RSSIs by commanding, based on the measured RSSIs, at least one of the implantable medical devices to modify the respective modulation level(s) at which the respective communication link(s) are amplitude modulated. Decreasing the variation of the RSSIs may result in substantial uniformity between the RSSIs. For example, the variation of the RSSIs may be less than 50%, and may even be less than 20%.

The implantable medical devices may be further configured for generating data (e.g., physiological data acquired from the patient by the implantable medical devices or operational data of the implantable medical devices) and sequentially amplitude modulating the communication links with the data by the implantable medical devices after the variation of the RSSI has been decreased, in which case, the telemetry controller may be further configured for amplitude demodulating the communication links to acquire the data from the implantable medical devices.

In one embodiment, the implantable medical devices are configured for respectively stored modulation indices that respectively set the modulation levels at which the implantable medical devices amplitude modulate the communication links, in which case, the telemetry controller may be configured for commanding the implantable medical device(s) to modify the respective modulation level(s) by commanding the implantable medical device(s) to modify the respective modulation index(ices).

In another embodiment, the telemetry controller is configured for decreasing the variation of the RSSIs by determining the lowest one of the RSSIs, selecting one of the implantable medical devices not associated with the lowest RSSI, and commanding the selected implantable medical device to modify the respective modulation level to an equalizing modulation level, such that the RSSI of the communication link amplitude modulated at the new modulation level by the selected implantable medical device matches the lowest RSSI.

In one example, the telemetry controller is configured for commanding the selected implantable medical device to modify the respective modulation level to the equalizing modulation level by decrementing the respective modulation level by a predetermined amount at least one time. In another example, the telemetry controller is configured for commanding the selected implantable medical device to modify the respective modulation level to the equalizing modulation level by approximating a modulation level at which the RSSI of the respective communication link amplitude modulated at the approximated modulation level by the selected implantable medical device is likely to match the lowest RSSI.

In one embodiment, the implantable medical devices may be configured for initially amplitude modulating the communication links at maximum modulation levels, in which case, the telemetry controller may be configured for commanding the selected implantable medical device to modify the respective modulation level to the equalizing modulation level by reducing the respective maximum modulation level to the respective equalizing modulation level. In another embodiment, the RSSI of the communication link amplitude modulated at the modified modulation level by the selected implantable medical device may be measured and compared with the lowest RSSI, and the modulation level modifying, RSSI measuring, and RSSI comparison functions may be repeated until the RSSI of the amplitude modulated communication link between the telemetry controller and the selected implantable medical device matches the lowest RSSI.

The telemetry controller may be further configured for selecting another one of the implantable medical device not associated with the lowest RSSI, and commanding the other selected implantable medical device to modify the respective modulation level to another equalizing modulation level, such that the RSSI of the communication link amplitude modulated at the other equalizing modulation level by the selected implantable medical device matches the lowest RSSI. The telemetry controller may be configured for repeating the implantable medical device selection and modulation level modification functions for all remaining ones of implantable medical devices not associated with the lowest RSSI.

In one embodiment, the telemetry controller comprises a primary coil, and a coil driver configured for applying a primary carrier signal having an envelope to the primary coil. Each of the implantable medical devices comprises a secondary coil on which a secondary carrier signal having an envelope may be induced in response to the application of the primary carrier signal on the primary coil, thereby establishing the respective communication link between the implantable medical device and the telemetry controller, and an uplink modulator configured for amplitude modulating (e.g., load modulating) the secondary carrier signal envelope at the respective modulation level, thereby inducing an amplitude modulation of the primary carrier signal envelope on the primary coil. Each of the implantable medical devices may further comprise a rectifier configured for rectifying and regulating the secondary carrier signal on the respective secondary coil for powering circuitry within the respective implantable medical device.

In this embodiment, the telemetry controller may further comprise an amplitude detector configured for detecting a peak-to-peak amplitude of the induced amplitude modulations of the primary carrier signal envelope, control circuitry configured for determining the RSSIs from the detected peak-to-peak amplitudes, and generating at least one command based on the measured RSSIs, and a downlink modulator configured for amplitude modulating the primary carrier signal envelope on the primary coil with the at least one command, thereby inducing an amplitude modulation of the secondary carrier signal envelope, encoded with the respective command, on the secondary coil of the at least one implantable medical device. Each of the implantable medical device(s) further comprises a downlink demodulator configured for amplitude demodulating the modulated secondary carrier signal envelope to acquire the respective command, and control circuitry configured for modifying the respective modulation level in accordance with the respective command.

Each of the medical devices may be configured for generating data, and the uplink modulator of each implantable medical device may be configured for amplitude modulating the secondary carrier signal envelope on the secondary coil with the respective data, thereby inducing an amplitude modulation of the primary carrier signal envelope, encoded with the data, on the primary coil of the telemetry controller. In this case, the telemetry controller may further comprise an uplink demodulator configured for amplitude demodulating the modulated primary carrier signal envelope to acquire the data. Such uplink demodulator may be configured for amplitude demodulating the modulated primary carrier signal envelope by detecting the modulated primary carrier signal envelope, and comparing the detected modulated primary carrier signal envelope to a threshold level. The amplitude of the threshold level may be between a minimum and a maximum of the modulated primary carrier signal envelope, and the amplitude of the threshold level may be centered between the minimum and the maximum of the modulated primary carrier signal envelope.

In accordance with a second aspect of the present inventions, a method of communicating between a telemetry controller and a plurality of medical devices implanted within a patient comprises respectively establishing communication links between the telemetry controller and the implanted medical devices, respectively amplitude modulating the communication links by the implanted medical devices at modulation levels, respectively measuring received signal strength indicators (RSSIs) of the amplitude modulated communication links for the implanted medical devices, and decreasing a variation of the RSSIs by modifying, based on the measured RSSIs, at least one modulation level at which the respective at least one communication link is amplitude modulated by the respective at least one implanted medical device, e.g., by sending at least one command from the telemetry controller. Decreasing the variation of the RSSIs may result in substantial uniformity between the RSSIs. For example, the variation of the RSSIs may be less than 50%, and may even be less than 20%.

The method may further comprise generating data (e.g., physiological data acquired from the patient by the implantable medical devices or operational data of the implantable medical devices) by the implanted medical devices, sequentially amplitude modulating the communication links with the data by the implanted medical devices after the variation of the RSSI has been decreased, and amplitude demodulating the communication links by the telemetry controller to acquire the data from the implanted medical devices.

One method further comprises storing modulation indices in the respective implanted medical devices, in which case, the communication links may be respectively amplitude modulated by the implanted medical devices in accordance with modulation indices, and modifying the modulation level(s) comprises modifying the respective modulation index(ices).

Decreasing the variation of the RSSIs may comprise determining the lowest one of the RSSIs, selecting one of the implanted medical device not associated with the lowest RSSI, and modifying the respective modulation level to an equalizing modulation level, such that the RSSI of the communication link amplitude modulated at the new modulation level by the selected implantable medical device matches the lowest RSSI. In one method, the communication links may be initially amplitude modulated by the implanted medical devices at maximum modulation levels, in which case, the respective modulation level may be modified to the equalizing modulation level by reducing the respective maximum modulation level to the respective equalizing modulation level.

In one example, modifying the respective modulation level to the equalizing modulation level may comprise decrementing the respective modulation level by a predetermined amount at least one time. In another example, modifying the respective modulation level to the equalizing modulation level comprises approximating a modulation level at which the RSSI of the respective communication link amplitude modulated at the approximated modulation level by the selected implantable medical device is likely to match the lowest RSSI.

Modifying the respective modulation level to the equalizing modulation level may comprise measuring the RSSI of the communication link amplitude modulated at the modified modulation level by the selected implantable medical device, comparing the measured RSSI with the lowest RSSI, and repeating the modulation level modifying, RSSI measuring, and RSSI comparison steps until the RSSI of the amplitude modulated communication link between the telemetry controller and the selected implantable medical device matches the lowest RSSI.

The method may further comprise selecting another one of the implanted medical device not associated with the lowest RSSI, and modifying the respective modulation level to another equalizing modulation level, such that the RSSI of the communication link amplitude modulated at the other equalizing modulation level by the selected implantable medical device matches the lowest RSSI. The implanted medical device selection and modulation level reduction steps may be repeated for all remaining ones of implanted medical devices not associated with the lowest RSSI.

The telemetry controller may have a primary coil and each of the medical devices may have a secondary coil, and coupling coefficients between the primary coil and the secondary coils may differ from each other. In this case, the communication links between the implanted medical devices and the telemetry controller may be established by applying a primary carrier signal having an envelope to the primary coil, thereby respectively inducing a secondary carrier signal having an envelope on each of the secondary coils, and the communication links may be amplitude modulated (e.g., load modulating) by the implanted medical devices by sequentially amplitude modulating each of the secondary carrier signal envelopes on the secondary coils, thereby inducing an amplitude modulation of the primary carrier signal envelope on the primary coil for the implanted medical devices. The method may further comprise generating power for each of the implanted medical devices from the respective secondary carrier signal.

The telemetry controller may send at least one command to the implanted medical device(s) to modify the modulation level(s) by amplitude modulating the primary carrier signal envelope on the primary coil with the command(s), thereby inducing an amplitude modulation of the secondary carrier signal envelope(s), encoded with the command(s), on the secondary coil(s) of the implanted medical device(s).

The method may further comprise generating data by the implanted medical devices, sequentially amplitude modulating the secondary carrier signal envelopes on the respective second coils with the data after the variation of the RSSIs has been decreased, thereby inducing an amplitude modulation of the primary carrier signal envelope, encoded with the data, on the primary coil for the implanted medical devices, and amplitude demodulating the modulated primary carrier signal envelope to acquire the data from the implanted medical devices. Amplitude demodulating the modulated primary carrier signal envelope may comprise detecting the modulated primary carrier signal envelope, comparing the detected modulated primary carrier signal envelope to a threshold level. The amplitude of the threshold level may be centered between a lowest and a maximum of the modulated primary carrier signal envelope.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings.

Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 4:
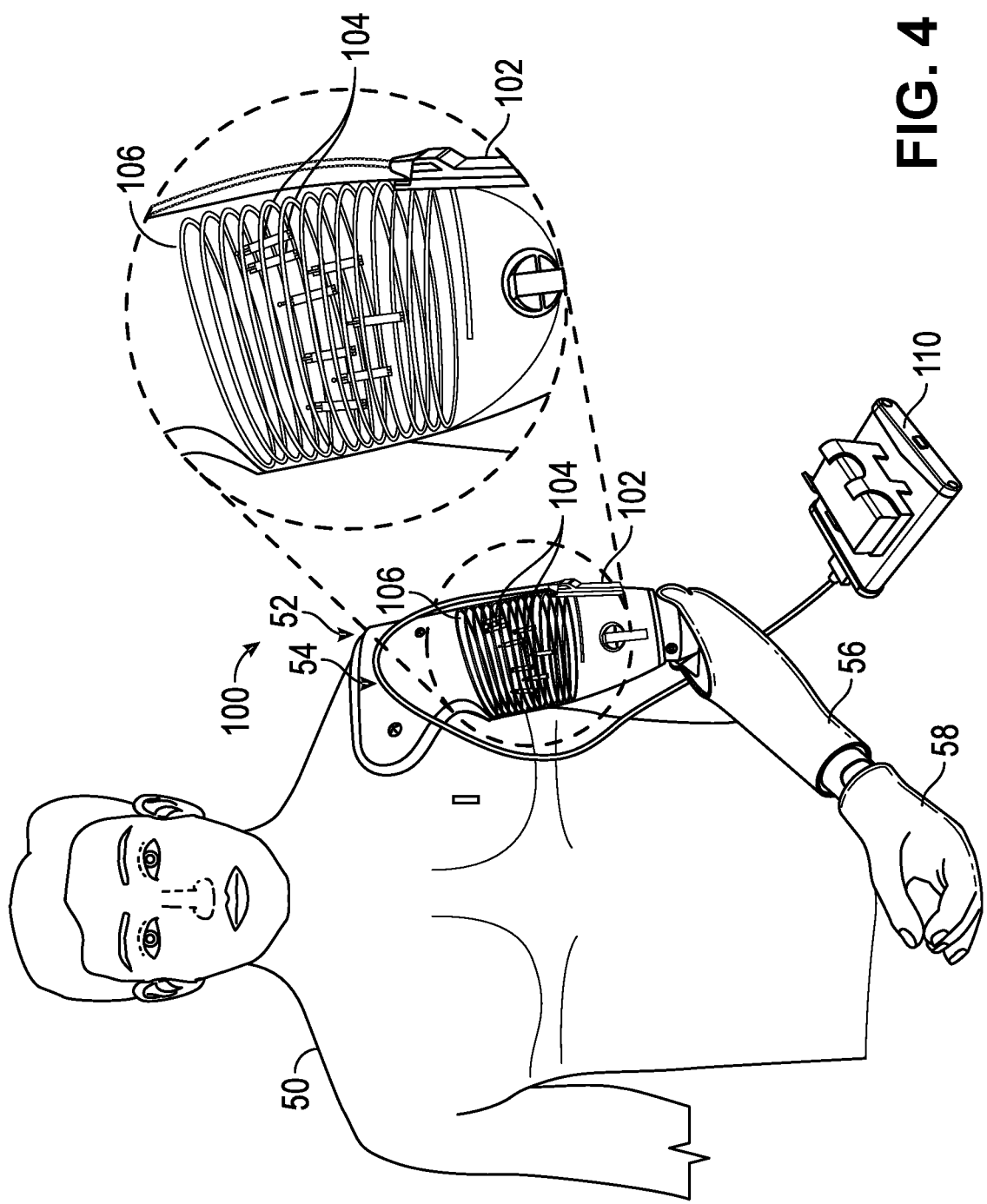
FIG. 4 is a pictorial of a prosthetic control system constructed in accordance with one embodiment of the present inventions.

Referring to FIG. 4, a medical system 100 constructed in accordance with one embodiment of the present inventions will now be described. The medical system 100 generally comprises an external telemetry controller (TC) 102 and a plurality of implantable medical devices 104. In the illustrated embodiment, the medical system 100 takes the form of a prosthetic control system.

In this case, the implantable medical devices 104 may take the form of sensor devices that are implanted within a residual portion of an amputated limb 52 of a patient 50 respectively adjacent muscles of interest for detecting muscle contraction, for example, by monitoring electromyogram (EMG) signals of the muscles of interest. The prosthetic control system 100 comprises a bionic prosthesis 54 having a prosthetic forearm 56 and prosthetic hand 58. The TC 102 may be incorporated into the bionic prosthesis 54, and is configured for delivering power to and receiving EMG data from the sensor devices 104. To facilitate power transfer and communications, the TC 102 comprises a primary coil 106, which may be incorporated into the socket portion of the bionic prosthesis 54 in a manner that it surrounds the sensor devices 104 implanted within the residual limb portion 52 of the patient 50. The TC 102 comprises power transfer and communication circuitry that inductively powers and communicates with the implanted sensor devices 104 via the primary coil 106.

The prosthetic control system 100 further comprises a prosthetic controller 110 coupled to the TC 102 via a cable 112 for receiving EMG data from TC 102, and is further coupled to motors (not shown) in the bionic prosthesis 54 to control movement of the prosthetic arm 56 and prosthetic hand 58. The prosthetic controller 110 may be worn by the patient 50, e.g., on the waist. The prosthetic control system 100 may further comprises one or more batteries (not shown), which may be physically integrated into the prosthesis 54 or otherwise contained in the prosthetic controller 110, for providing power to the circuitry within the TC 102 and prosthetic controller 110.

Thus, the prosthetic control system 100 allows the patient 50 to control the prosthetic forearm 56 and prosthetic hand 58 by attempting to contract the muscles in the residual limb portion 52. Different muscles or different portions of the muscles would correspond to independently movable parts, such as the elbow, wrist, and fingers of the bionic prosthesis 54. When a sensor device 104 detects contraction in a muscle or portion of a muscle, it communicates the resulting EMG data to the prosthetic controller 110 via the TC 102 that the muscle or portion of a muscle was contracted. The EMG data identifies the muscle that has been contracted, as well as the magnitude of the contraction. The prosthetic controller 110 then controls the bionic prosthesis 54 to move the independently movable part that corresponds with the muscle that was contracted according to the magnitude of the contraction.

Although the TC 102 and prosthetic controller 110 are shown as being separate physical units in FIG. 4, it should be appreciated that the TC 102 and prosthetic controller 110 may be integrated into a single physical unit that is incorporated into the prosthesis 54 or otherwise worn by the patient 50. It should also be appreciated that although the prosthetic control system 100 has been described as being a prosthetic control system, the prosthetic control system 100 can be any medical system that performs a diagnostic or therapeutic function. Likewise, although the implantable medical devices 102 are described as being EMG sensors, the implantable medical devices 102 may take the form of any medical device that performs a diagnostic or therapeutic function. Furthermore, although the TC 102 is described herein as being external to the patient 50, it should be appreciated that the TC 102 may take the form of, or otherwise be incorporated into, an implantable device that communicates with the other sensor devices 104.

Each of the sensor devices 104 may take the form of a miniaturized cylindrical sensing device, with the circuitry being implemented as a sub-assembly on a single-chip integrated circuit mounted on a ceramic substrate sandwiched between two halves of a cylindrical magnetic core around which the inductive coil is wound. The electronics are encapsulated in a cylindrical ceramic package that includes two metal endcaps at opposite ends of the ceramic package that serve as the differential recording electrodes. Such an implantable sensor device allows the EMG signals to be detected at the implantation site of this device. An example of such an implantable sensor device 104 is the IMES® device manufactured by The Alfred E. Mann Foundation for Scientific Research and described in Implantable Myoelectric Sensors (IMESs) for Intramuscular Electromyogram Recording, IEEE Trans Biomed Eng. 2009 Jan., pp. 159-171. In an alternative embodiment, the sensor device 104 may include a lead (not shown) on which the electrodes are carried, so that EMG signals can be detected at a location remote from the implantation site of the body of the device.

Figure 5:
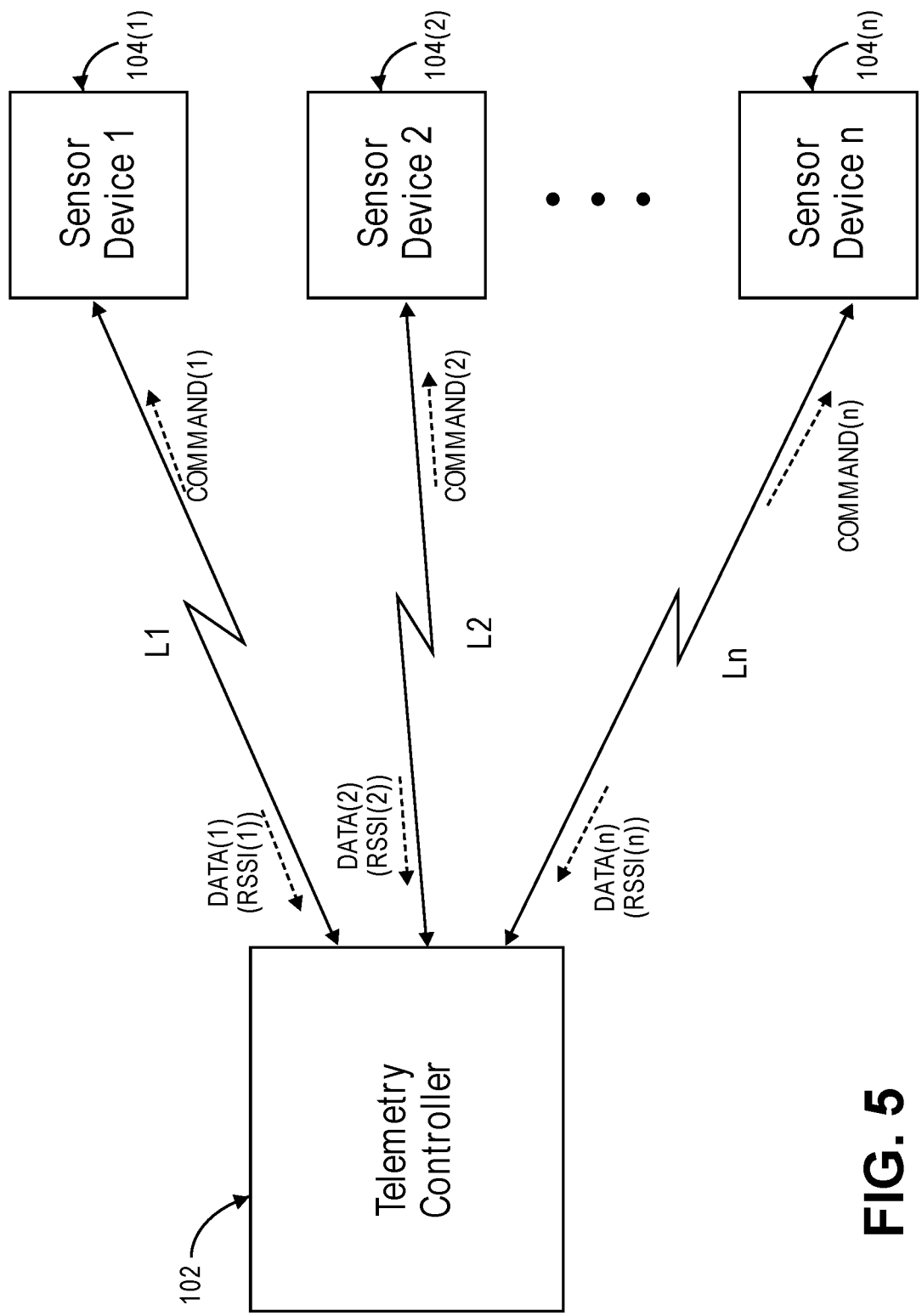
FIG. 5 is a block diagram of a telemetry controller and a plurality of sensor devices for use in the prosthetic control system of FIG. 4, particularly showing the transmission of data and commands between the telemetry controller and the sensor devices.

Referring now to FIG. 5, the TC 102 may establish communication links L1-Ln between the respective sensor devices 104(1)-104(n) and the TC 102. Thus, the sensor devices 104(1)-104(n) may send DATA(1)-DATA(n) to the TC 102 by serially (one at a time) amplitude modulating the respective communication links L1-Ln at defined modulation levels with the DATA(1)-DATA(n), and the TC 102 may receive the DATA(1)-DATA(n) from the sensor devices 104(1)-104(n) by demodulating the respective communication links L1-Ln to acquire the DATA(1)-DATA(n). Such modulation levels may be defined by, e.g., modulation indices stored in the sensor devices 104(1)-104(n). Likewise, the TC 102 may send COMMANDS(1)-COMMANDS(n) to the sensor devices 104(1)-104(n) by amplitude modulating the respective communication links L1-Ln at a defined modulation level with the COMMANDS(1)-COMMANDS(n), and the sensor devices 104(1)-104(n) may receive the COMMANDS(1)-COMMANDS(n) from the TC 102 by demodulating the respective communication links L1-Ln to acquire the COMMANDS(1)-COMMANDS (n).

It should be appreciated that, for the purposes of this specification, "amplitude modulation" refers to any modulation where the peak-to-peak amplitude of a carrier signal is modified, and includes, e.g., such modulation techniques as AM, ASK, FSK, PSK, etc. In the specific embodiment illustrated herein, the sensor devices 104(1)-104(n) amplitude modulate secondary carrier signals on respective secondary coils using load modulation.

Figure 1:
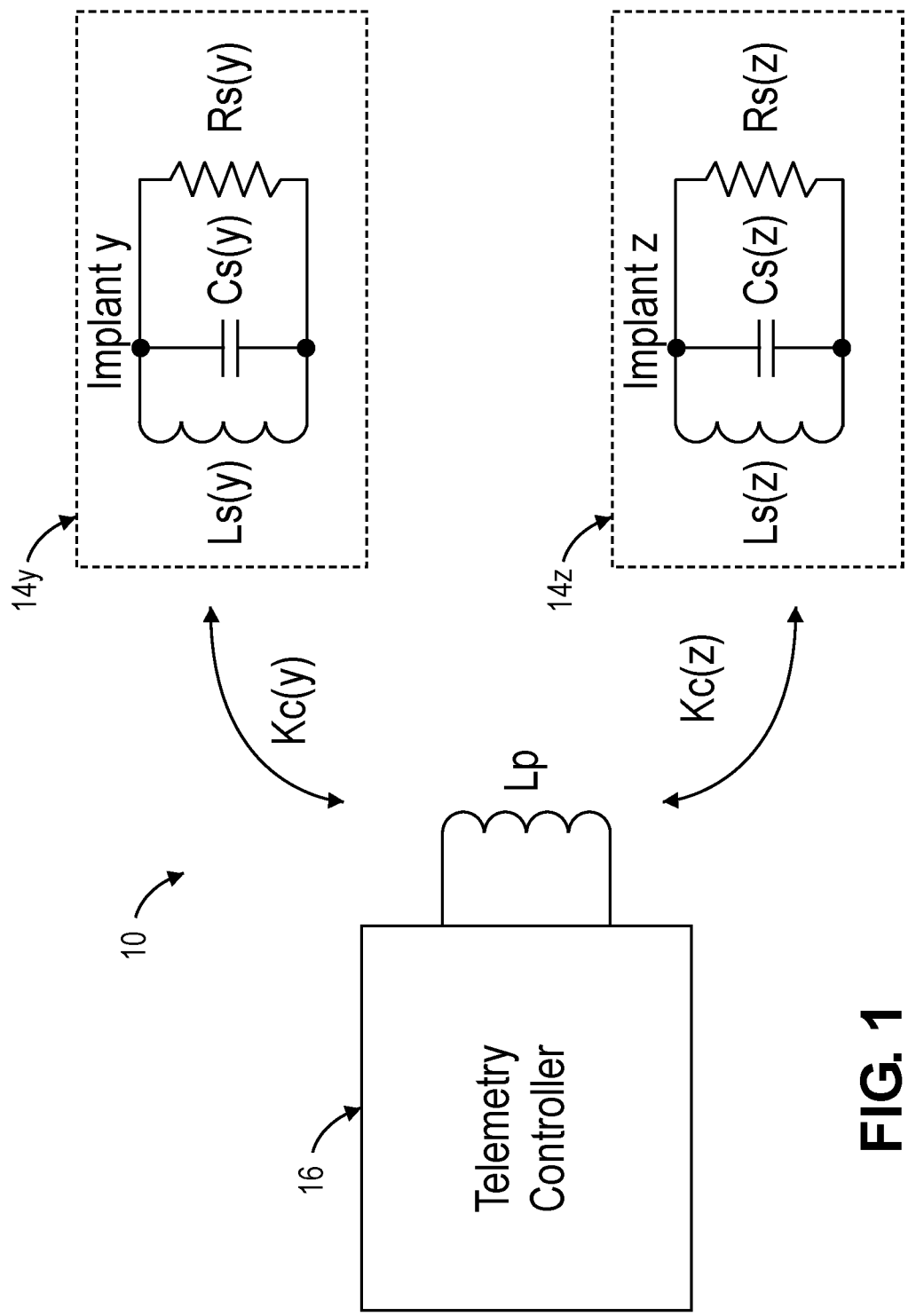
FIG. 1 is a block diagram of a prior art power/data transfer system for powering and communicating with implantable medical devices via a telemetry controller.
Figure 2:
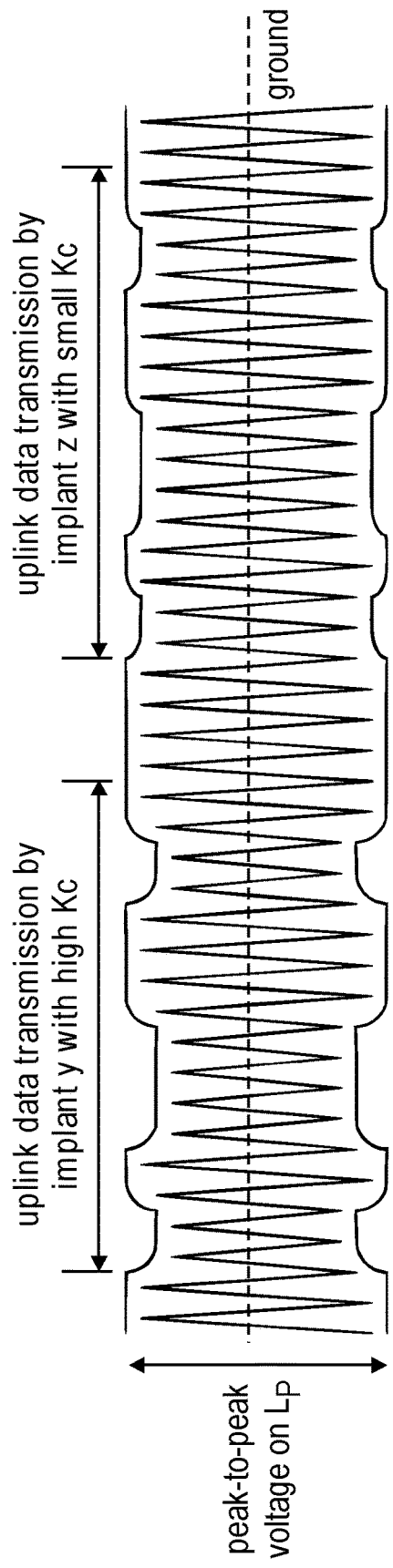
FIG. 2 is a diagram of a primary carrier signal on a primary coil of the telemetry controller that has been modulated in accordance with an amplitude shift keying (ASK) technique with uplink data received from the medical devices of FIG. 1.
Figure 3A:
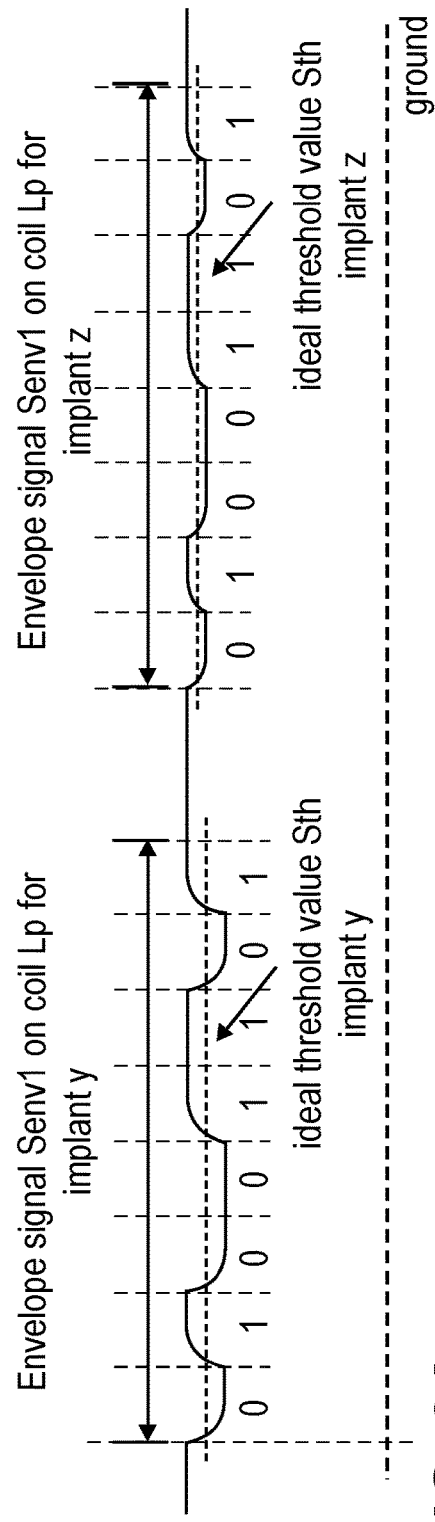
FIG. 3a is a diagram of an envelope signal detected from the modulated primary carrier signal of FIG. 2.
Figure 3B:
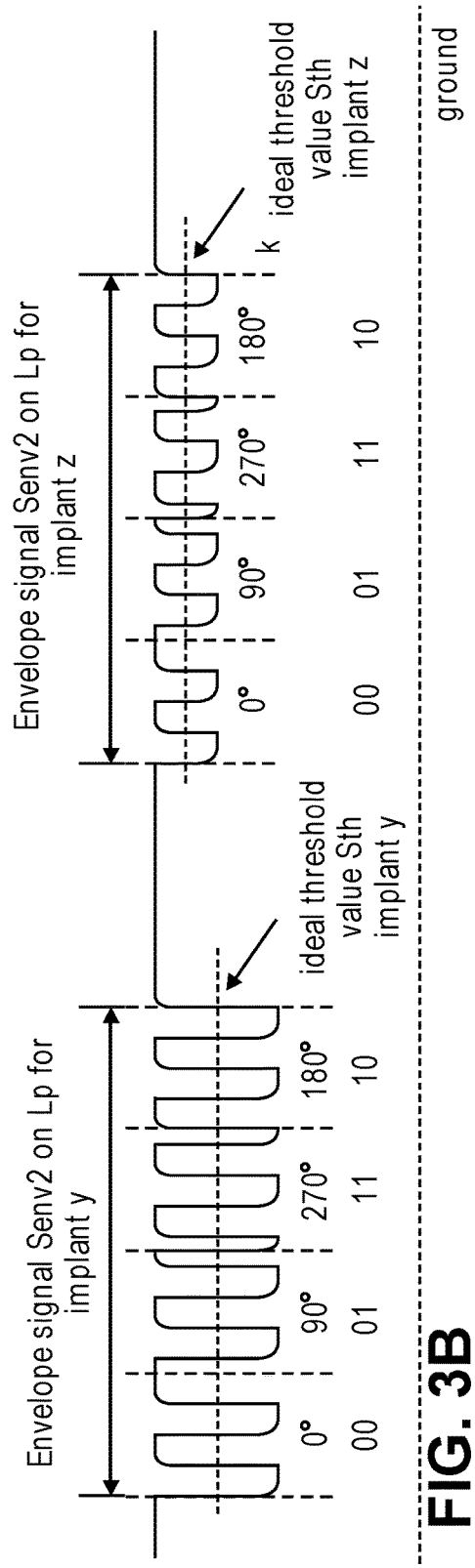
FIG. 3b is a diagram of an envelope signal alternatively detected from a primary carrier signal that has been modulated in accordance with a phase shift keying (PSK) technique with uplink data received from the medical devices of FIG. 1.
Figure 3C:
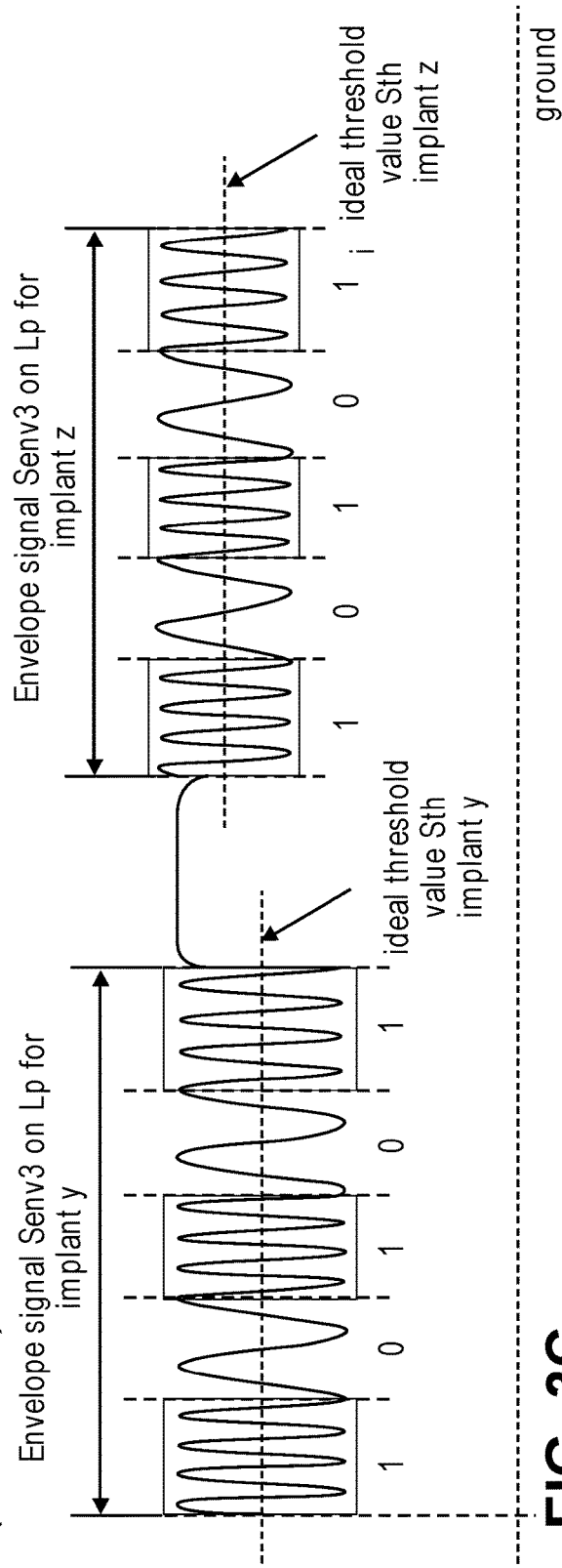
FIG. 3c is a diagram of an envelope signal alternatively detected from a primary carrier signal that has been modulated in accordance with a frequency shift keying (FSK) technique with uplink data received from the medical devices of FIG. 1.

Although amplitude modulations may be applied to the communication links L1-Ln by the respective sensor devices 104(1)-104(n) at the same modulation level, the modulations may be detected by the TC 102 at different levels, which may require more complicated demodulation circuitry and/or slower data transmission rate to accurately acquire the data from the communication links L1-Ln. For example, as discussed in the background of the invention with respect to FIGS. 1-3, if the communication links L1-Ln are inductive in nature, the coupling coefficients Kc1-Kcn between the primary coil 106 of the TC 102 and respective secondary coils 108(1)-108(n) of the sensor devices 104(1)-104(n) may differ from each other, such that without compensation, the load modulations of the secondary carrier signal envelopes Senv at the same modulation level will induce amplitude modulations on the primary carrier signal envelope Penv (i.e., the peak-to-peak amplitude of the primary carrier signal envelope Penv will be different for the sensor devices 104) at different levels.

Significantly, the prosthetic control system 100 is capable of equalizing the levels of the amplitude modulations of the communication links L detected by the telemetry controller 102 by modifying at least one modulation level at which the respective sensor device(s) 104 amplitude modulate the respective communication link(s) L to equalizing modulation level(s), e.g., by modifying the modulation indices corresponding the modulation level(s). The prosthetic control system 100 accomplishes this function by focusing on the received signal strength indicators RSSI(1)-RSSI(n) of the amplitude modulated communication links L as a means for determining the equalizing modulation levels at which the sensor devices 104 amplitude modulate the communications links L.

To this end, the TC 102 is configured for respectively measuring the RSSI(1)-RSSI(n) of the amplitude modulated communication links L, and decreasing a variation of the RSSIs by commanding, based on the determined RSSI(1)-RSSI(n), at least one of the sensor devices 104 (e.g., by sending commands over the communication links L to the sensor devices 104) to modify the respective modulation level(s) at which the respective communication link(s) L are amplitude modulated to equalizing modulation level(s), as will be described in further detail below. For example, the TC 102 may be configured for determining the lowest one of the RSSI(1)-RSSI(n), selecting those sensor devices 104 not associated with the lowest RSSI, (i.e., those sensor devices 104 associated with the communication links L having RSSI's higher than the lowest RSSI, and commanding the selected sensor devices 104 to reduce the respective modulation levels (e.g., by reducing the modulation indices) to equalizing modulation levels, such that the RSSI(1)-RSSI(n) of the amplitude modulation communication links L between the TC 102 and the selected sensor devices 104 match the RSSI. In this manner, the RSSI(1)-RSSI(n) associated with the communication links L amplitude modulated by the respective sensor devices 104 may be substantially uniform. For example, the variation of these RSSI(1)-RSSI (n) may be less than 50%, and preferably less than 20%.

Figure 6A:
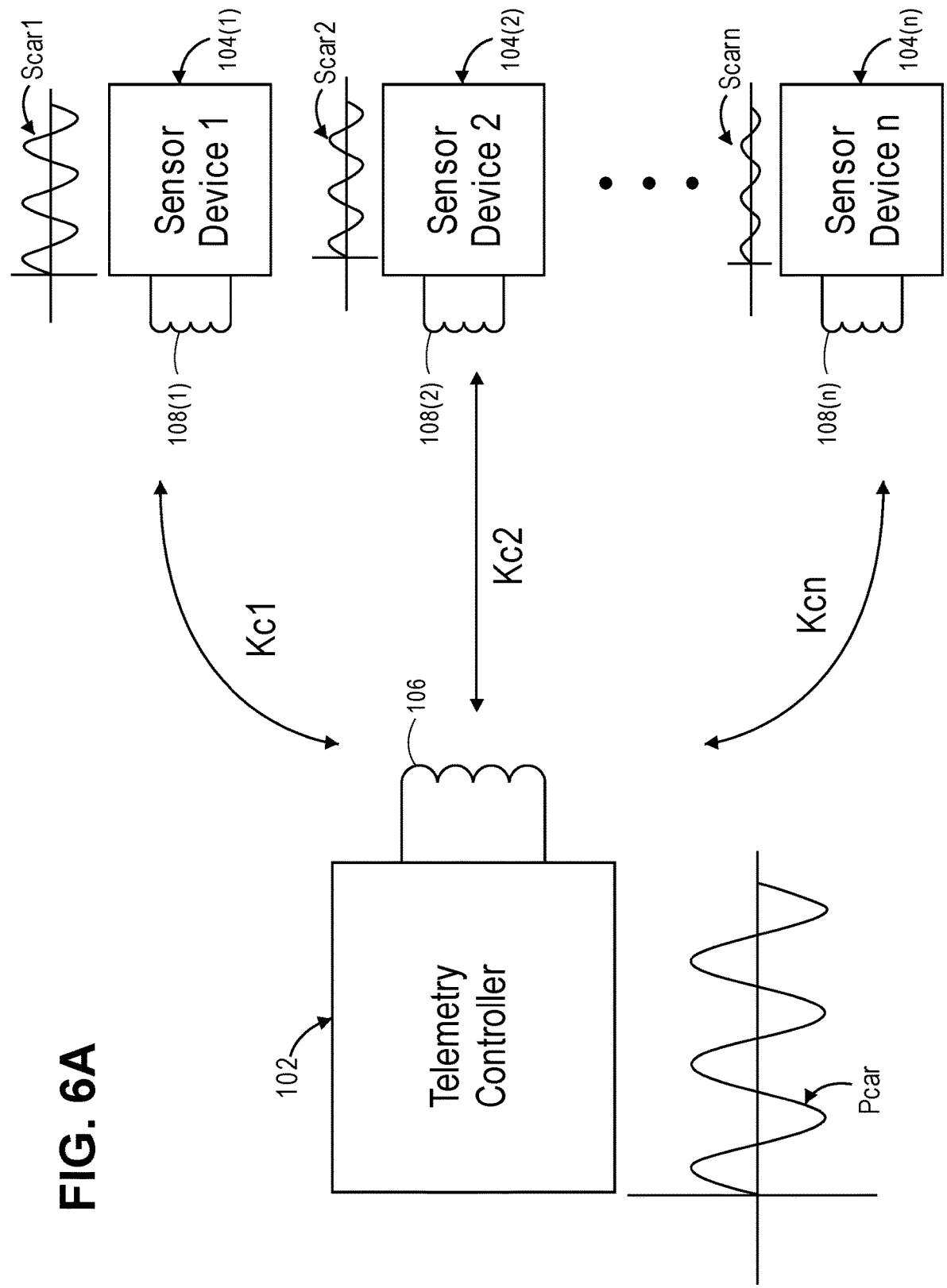
FIG. 6a is a block diagram of the telemetry controller and sensor devices of FIG. 5, particularly showing the induction of different secondary carrier signals on the secondary coils of the sensor devices in response to the application of a primary carrier signal on the primary coil of the telemetry controller.
Figure 6B:
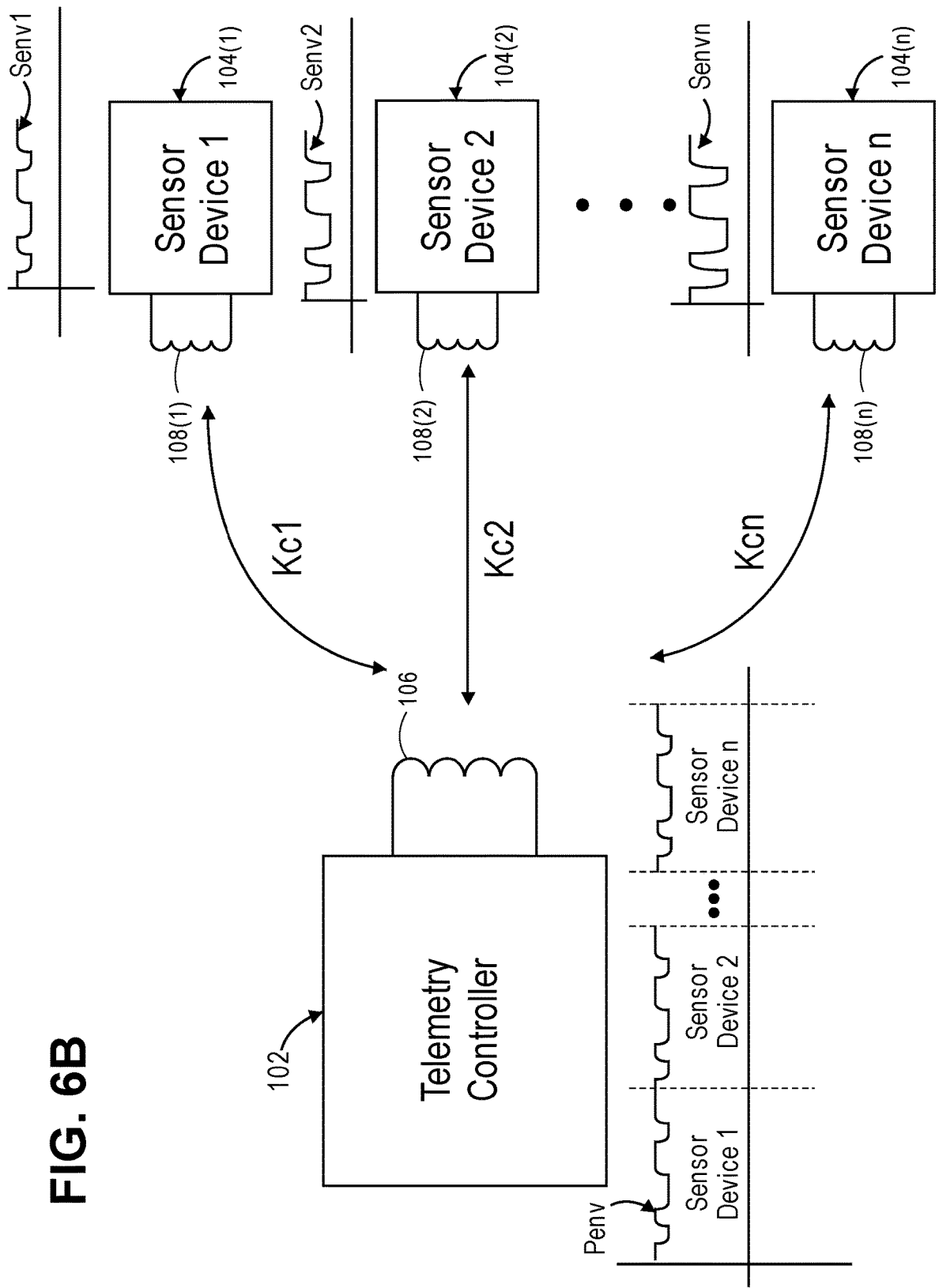
FIG. 6b is a block diagram of the telemetry controller and sensor devices of FIG. 6a, particularly showing the induction of amplitude modulations on the primary carrier signal on the primary coil of the telemetry coil in response to the application of amplitude modulations on the secondary coils of the respective sensor devices.

Referring to FIGS. 6a and 6b, one embodiment for equalizing the levels of the amplitude modulations of communication links L detected by the telemetry controller 102 will be described. In this embodiment, the communication links L are inductive, and thus, the TC 102 may establish the inductive communication links L1-Ln by applying an exemplary unmodulated primary alternating current (AC) carrier signal Pcar to the primary coil 106, which induces exemplary unmodulated secondary AC carrier signals Scar1-Scarn on secondary coils 108 of respective sensor devices 104(1)-104(n), thereby establishing these communication links L1-Ln, as illustrated in FIG. 6a.

The sensor devices 104(1)-104(n) amplitude modulate the respective inductive communication links L1-Ln at defined modulation levels with data by load modulating the envelopes Senv1-Senvn of the secondary carrier signals Scar on the respective secondary coils 108 at these defined modulation levels in accordance with the data, thereby inducing an amplitude modulation of the envelope Penv of the primary carrier signal Pcar (encoded with the data) on the primary coil 106, which can then be demodulated by the TC 102 to acquire the data from the sensor devices 104, as illustrated in FIG. 6b.

As previously discussed, different coupling coefficients Kc1-Kcn between the primary coil 106 and respective secondary coils 108 may result in the induction of amplitude modulations on the primary carrier signal envelope Penv at different levels (i.e., the peak-to-peak amplitude of the primary carrier signal envelope Penv will be different for the sensor devices 104). The prosthetic control system 100 equalizes the levels of the induced amplitude modulations of the primary carrier signal envelope Penv on the primary coil 106 of the TC 102 amongst the sensor devices 104 by modifying at least one modulation level at which the respective sensor device(s) 104 load modulate the respective secondary carrier signal envelope(s) Senv on the secondary coil(s) 108 to equalizing modulation level(s).

As there shown, the load modulations of the secondary carrier signal envelopes Senv are at different modulation levels, such that amplitude modulations of the primary carrier signal envelope Penv will be substantially equal for the respective sensor devices 104. As a general rule, the load modulations of the secondary carrier signal envelopes Senv1-Senvn should have modulation levels that vary in an inversely varying relationship to the coupling coefficients Kc1-Kcn between the respective secondary coils 104(1)-104 (n) and the primary coil 102. In other words, as a coupling coefficient Kc between the primary coil 106 and a particular secondary coil 108 increases, the modulation level of the load modulated secondary carrier signal envelope Senv on the secondary coil 108 should be decreased, and conversely, as a coupling coefficient Kc between the primary coil 106 and a particular secondary coil 108 decreases, the modulation level of the load modulated secondary carrier signal envelope Senv on the secondary coil 108 is increased.

In an effort to equalize the levels of the induced amplitude modulations of the primary carrier signal envelope Penv on the primary coil 106 of the TC 102 amongst the sensor devices 104, the prosthetic control system 100 modifies the modulation level(s) at which the respective sensor device(s) 104 load modulate the respective secondary carrier signal envelope(s) Senv on the secondary coil(s) 108 to the equalizing modulation level(s). In particular, the TC 102 is configured for respectively measuring the RSSIs of the amplitude modulated communication links L, and decreasing a variation of the RSSIs by commanding, based on the determined RSSIs, at least one of the sensor devices 104 to modify the respective modulation level(s) at which the respective communication link(s) L are load modulated to the equalization modulation level(s).

In the illustrated embodiment, the TC 102 amplitude modulates the respective communication links L1-Ln with commands by amplitude modulating the primary carrier signal envelopes Penv1-Penvn on the primary coil 106 in accordance with the commands, thereby inducing amplitude modulations of the secondary signal envelopes Senv (encoded with the commands) on the secondary coils 108 of the sensor devices 104, which can then be demodulated by the sensor devices 104 to acquire the respective commands from the TC 102. The sensor devices 104 may then modify the defined modulation levels in accordance with the commands, e.g., by modifying the modulation indices stored in the sensor devices 104.

In this manner, variation of the modulation magnitude of the modulated primary carrier signal envelope Penv on the primary coil 106 between the sensor devices 104 will be decreased to compensate for the different coupling coefficients Kc1-Kcn (and secondarily, to compensate for any variation in tuning tolerances) between the primary coil 106 and the secondary coils 108. Preferably, the primary carrier signal envelope Penv is substantially uniformly amplitude modulated for the implanted sensor devices 104. For example, a variation in the induced amplitude modulation of the primary carrier signal envelope Penv between the implanted sensor devices 104 is less than 50%, and preferably less than 20%.

Figure 7:
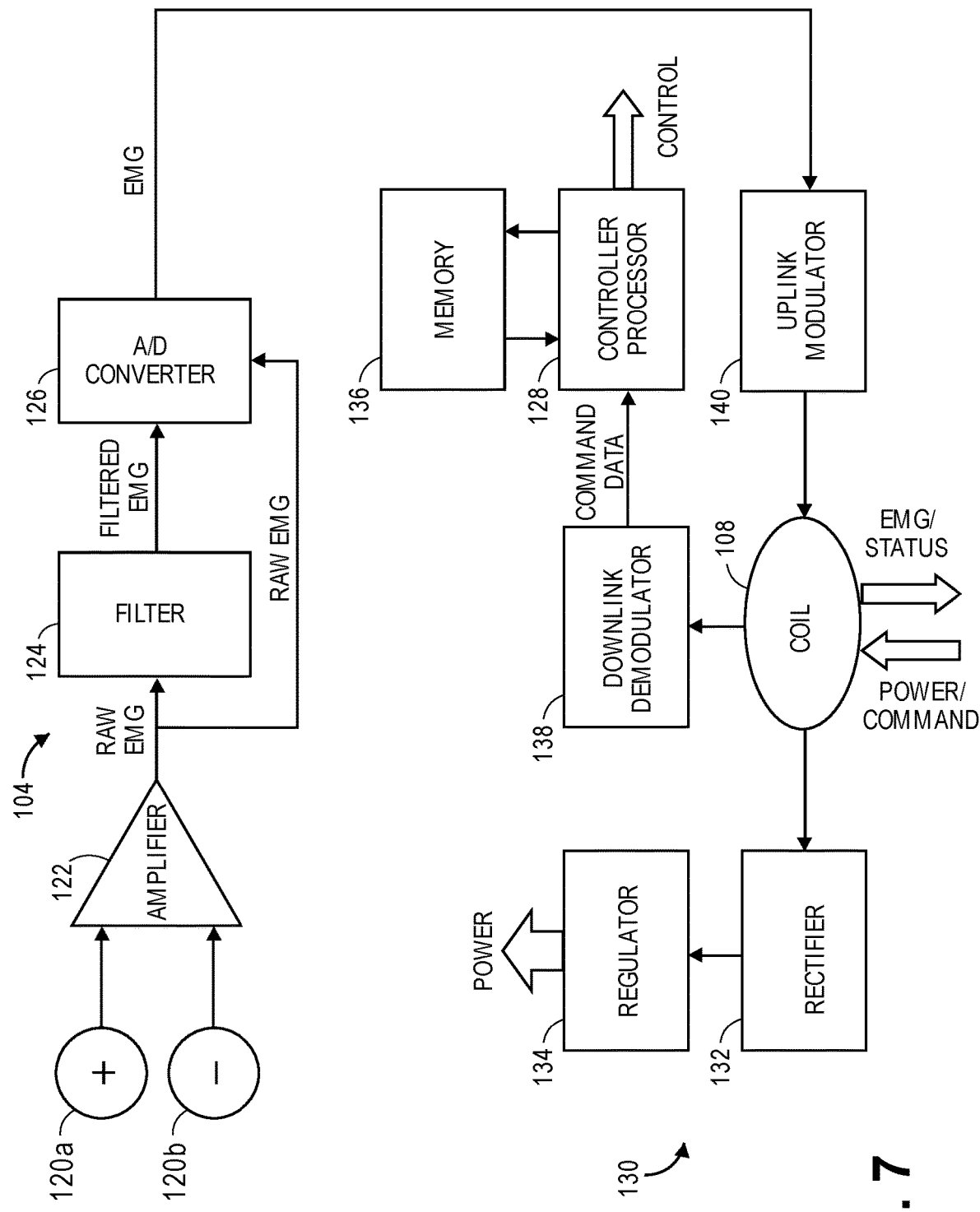
FIG. 7 is a block diagram of one of the sensor devices illustrated in FIGS. 6a and 6b.

Referring now to FIG. 7, each sensor device 104 is capable of sensing EMG signals. To this end, the sensor device 104 comprises two differential recording electrodes 120a, 120b configured for sensing electrical activity within the muscle fibers in which the sensor device 104 is implanted and outputting a raw analog EMG signal.

In alternative embodiments, the sensor device 104 may sense electrical impedance, field potential, evoked potential from nerves, temperature, tension, translucence, reflectance, pH, motion, inertial, chemical, respiration, vascular pulsation, heartbeat, ECG, EKG, EEG, EOG, etc.

The sensor device 104 further comprises one or more adjustable gain amplifiers 122 configured for amplifying the EMG signal; a filter 124 configured for obtaining an envelope, integrating, or sampling the EMG signal; an analog-to-digital converter (A/D) converter 126 configured for selectively transforming either the raw EMG signal output from the amplifier(s) 122 or the filtered EMG signal output from the filter 124 into a digitized EMG signal; and a controller/processor 128 (e.g., command processor, frame generator, PLL logic, command decoder, and error correction circuitry) configured for controlling and operating the sensor device 104 in accordance with commands received from the TC 102. The filter 124 can also be realized digitally, in which case, the filter 124 would be placed after the A/D converter 126.

The sensor device 104 further comprises telemetry/power circuitry 130 configured for receiving commands and power from the TC 102 and transmitting the EMG signal (either raw or filtered) to the TC 102. In the illustrated embodiment, the sensor device 104 utilizes a robust half-duplex data link for transmitting the filtered or raw EMG signal to the TC 102 and receiving command data from the TC 102.

To this end, the telemetry/power circuitry 130 comprises the aforementioned secondary coil 108 on which the secondary carrier signal is induced in response to the application of the primary carrier signal on the primary coil 106 of the TC 102. The telemetry/power circuitry 130 utilizes secondary carrier signal as both a source of power and as a downlink/uplink carrier signal. The telemetry/power circuitry 130 further comprises a rectifier 132 and power regulator 134 for rectifying and regulating the inductive carrier signal received at the secondary coil 108 for powering the circuitry of the sensor device 104. In alternative embodiments, the sensor device 104 may include a rechargeable battery (not shown) for storing the electrical energy, or a non-rechargeable battery, in which case, power may be supplied to the circuitry of the sensor device 104 without connection to the TC 102. In this case, the sensor device 104 may further comprise memory 136 for storing the EMG data that can be subsequently transmitted via a dedicated communication coil upon interrogation of the sensor device 104 by the TC 102.

The telemetry/power circuitry 130 further comprises a downlink demodulator 138 configured for demodulating command data received from the TC 102 from the secondary carrier signal envelope at the secondary coil 108. In the illustrated embodiment, the downlink demodulator 138 is a demodulator that demodulates the secondary carrier signal envelope to acquire the command data by measuring the amplitude variations of the secondary carrier signal envelope.

The telemetry/power circuitry 130 further comprises an uplink modulator 140 configured for load modulating the secondary carrier signal envelope on the secondary coil 108 at a pre-defined modulation level with the raw or filtered EMG received from the A/D converter 126, thereby inducing an amplitude modulation of the primary carrier signal envelope on the primary coil 106. In optional embodiments, operational status data can be transmitted by the sensor device 104 to the external control unit 16 via the secondary coil 108 to provide, for example, battery status information or other operational information of the sensor device 104, in which case, the uplink modulator 140 may be configured for load modulating the secondary carrier signal envelope on the secondary coil 108 at the pre-defined modulation level with the operational status data. In the alternative case wherein the implantable medical device is a therapeutic device, such as a neurostimulator, the operational status data may be include electrical measurements made by the neurostimulator while stimulating a neuromuscular pathway.

As briefly discussed above, the controller/processor 128 is configured for controlling and operating the sensor device 104 in accordance with commands received from the TC 102. More significant to the present inventions, one of the commands received from the TC 102 may include an instruction to modify a modulation index, or may alternatively comprise a modulation index, that defines the modulation level at which the secondary carrier signal envelope is load modulated by the uplink modulator 140. The modulation index may be, e.g., an integer within a defined range, e.g., between 1 and 35. As such, the modulation level may accordingly be incrementally adjusted, with the modulation level increasing as the modulation index increases. The controller/processor 128 may store the current modulation index in the memory 136.

Figure 8A:
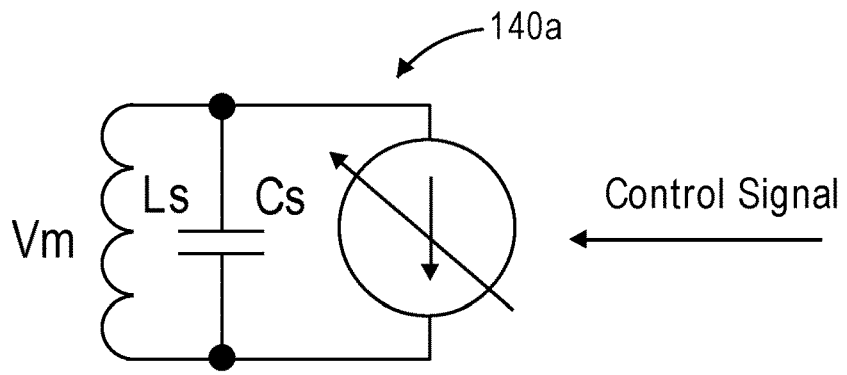
FIG. 8a is a schematic illustrating one type of load modulation technique used in the sensor device of FIG. 7 by varying the loading current on the secondary coil Ls.
Figure 8B:
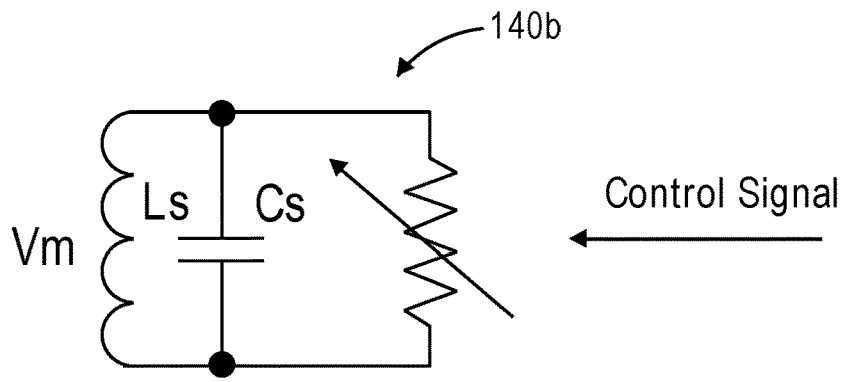
FIG. 8b is a schematic illustrating another type of load modulation technique used in the sensor device of FIG. 7 by varying the loading resistance on the secondary coil Ls.
Figure 8C:
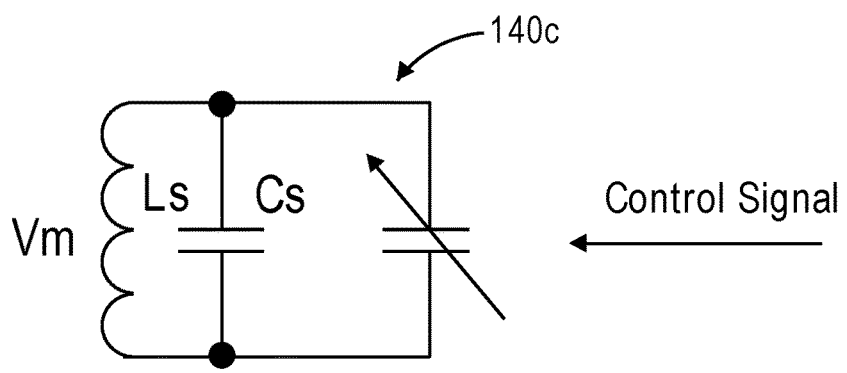
FIG. 8c is a schematic illustrating still another type of load modulation technique used in the sensor device of FIG. 7 by varying the equivalent capacitance of the capacitor Cs.

In the illustrated embodiment, the uplink modulator 140 may take the form of a digitally-controlled variable current source 140a, the load modulation level of which can be set by the controller/processor 128, as illustrated in FIG. 8a. The variable current source 140a is controlled via a modulating digital control signal output by the controller/processor 128, such that a modulation voltage Vm (i.e., a change in the voltage across the secondary coil Ls) is selected. As the current output of the current source 140a increases, the modulation voltage Vm increases. Alternatively, the uplink modulator 140 may take the form of a digitally-controlled variable resistor 140b, the load modulation level of which can be set by the controller/processor 128, as illustrated in FIG. 8b. The variable resistor 140b is controlled via a digital signal output by the controller/processor 128, such that the modulation voltage Vm is selected. As the resistance of the variable resistor 140b decreases, the modulation voltage Vm increases. Alternatively, the uplink modulator 140 may take the form of a digitally-controlled variable capacitor 140c, the modulation level of which can be set by the controller/processor 128, as illustrated in FIG. 8c. The variable capacitor 140c is controlled via a digital signal output by the controller/processor 128, such that the modulation voltage Vm is selected. As the capacitance of the variable capacitor 140c decreases, the modulation voltage Vm increases. Although the modulation level of the uplink modulator 140 is described herein as being digitally-controlled, it should be appreciated that load modulation level of the uplink modulator 140 may be analog-controlled.

Figure 9:
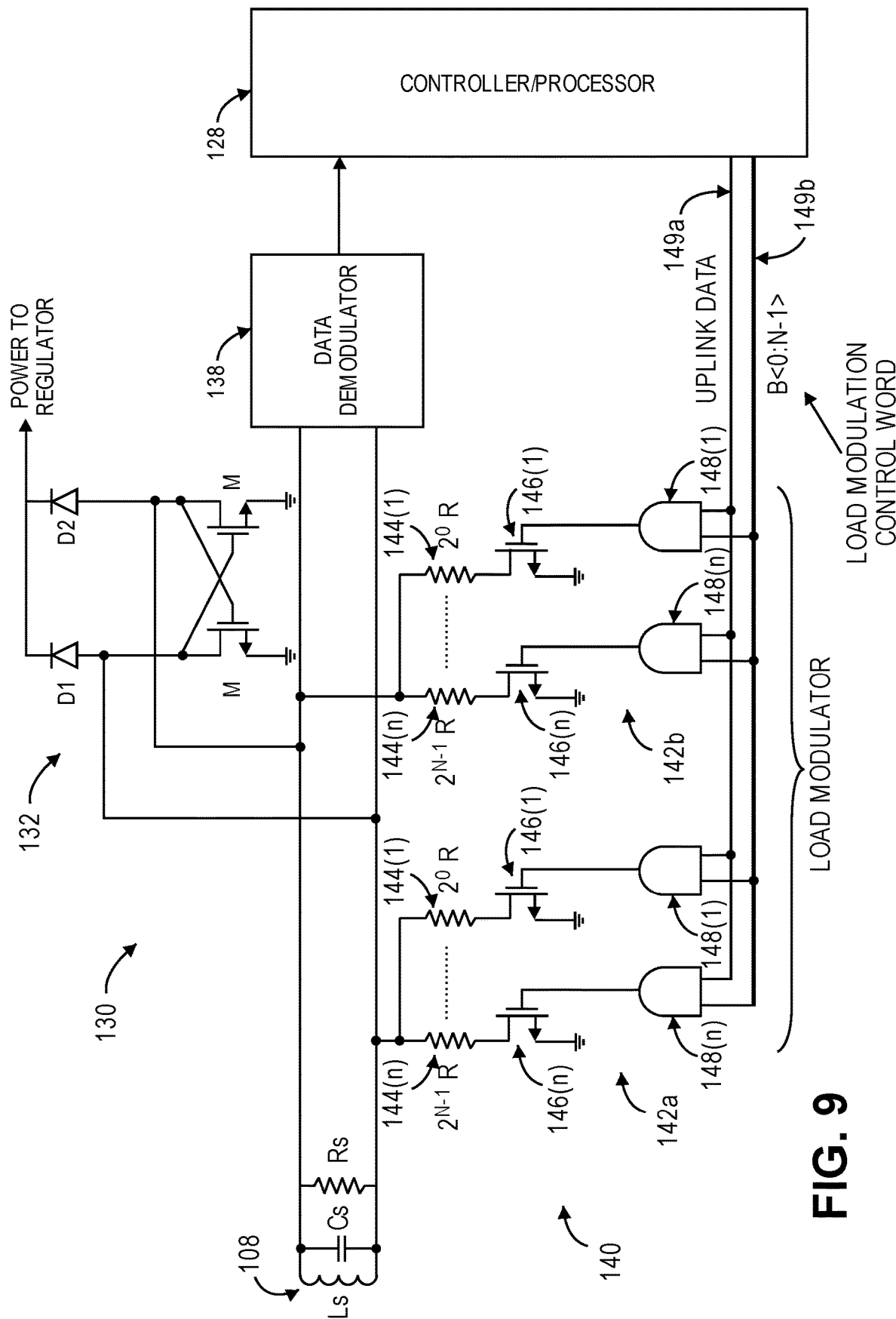
FIG. 9 is a schematic of telemetry/power circuitry of the sensor device of FIG. 7.

Referring now to FIG. 9, a detailed implementation of the telemetry/power circuitry 130 of the sensor device 104 will be described. In a conventional manner, the secondary coil 108 is represented by inductance Ls, and is combined in parallel with a capacitance Cs to form a receiver LC tank circuit that is inductively linked to corresponding transmitter LC tank circuit comprising the primary coil 106 and capacitance (not shown) at the TC 102. The receiver LC tank circuit and transmitter LC tank circuit are tuned to resonate at the frequency of the carrier signal generated by the TC 102, such that there is no parasitic reaction between the respective LC tank circuits.

The rectifier 132 is a conventional rectifier diode with cross-coupled NMOS transistors coupled across the receiver LC tank circuit to rectify the secondary carrier signal, and that delivers the rectified carrier signal to the regulator 134 for powering the circuitry. The positive portion of the secondary carrier signal is conducted through diode D1 to the regulator 134, while reverse biasing diode D1 via transistor M1, and the negative portion of the secondary carrier signal is conducted through diode D2 to the regulator 134, while reverse biasing diode D2 via transistor M2.

In the embodiment illustrated in FIG. 9, the uplink modulator 140 takes the form of a pair of digitally-controlled variable resistors 142a, 142b respectively coupled to the positive and negative terminals of the secondary coil 108, although in alternative embodiments, the uplink modulator 140 may take the form of a pair of digitally-controlled variable current sources or a pair of digitally controlled variable capacitors.

Each of the digitally-controlled variable resistors 142a, 142b comprises a series of resistor banks 144(1)-144(n) of varying resistances that can be selectively turned on and off via an N-bit load modulation control word by the controller/processor 128. In the illustrated embodiment, the total resistance of each of the resistor banks 144(1)-144(n) respectively comprises a unit value of $2^{N-1}$, such that the first resistor bank 144(1) has a total unit resistance value of $2^0 R$ (i.e., R), the second resistor bank 144(2) has a total unit resistance value of $2^1 R$ (i.e., 2R), the third resistor bank 144(3) has a total unit resistance value of $2^2 R$ (i.e., 4R), the fourth resistor bank 144(4) has a total unit resistance value of $2^4 R$ (i.e., 16R), and so forth. The variable resistor 140b further comprises a series of switches 146(1)-146(n) (e.g., transistors) coupled between the respective resistor banks 146(1)-146(n) and ground, and a series of AND gates 148(1)-148(n) coupled to the control terminals or gates of the respective switches 146(1)-146(n). The controller/processor 128 is coupled to one input terminal of the respective AND gates 148(1)-148(n) via an uplink data line 149a, and to the other input terminal of the respective AND gates 148(1)-148(n) via a modulation level control line 149b.

Thus, the secondary carrier signal envelope on the secondary coil 108 can be load modulated with data on the uplink data line 149a, with the modulation level being simultaneously selected with data on the modulation level control line 149b. That is, when a bit value (in this case, a binary "1") is applied to both input terminals of selected ones of the AND gates 146 of the variable resistors 142a, 142b, the corresponding switches 146 are closed, which turns on the corresponding resistor banks 144, and when a different bit value (in this case, a binary "0") is applied to either of the input terminals of selected ones of the AND gates 148 of the variable resistors 142a, 142b, the corresponding switches 146 are opened, which turns off the corresponding resistor banks 144. It can be appreciated from this that data on the modulation level control line 149b sets the modulation level of the uplink modulator 140 by allowing selected ones of the resistor banks 144 to be alternately turned on and off via the data on the uplink data line 149a, while preventing remaining ones of the resistor banks 144 from being alternately turned on and off via the data on the uplink data line 149a (i.e., the resistor banks 144 not selected for modulation will remain turned off regardless of the instant bit value on the uplink data line 149a).

The data on the uplink data line 149a will be a series of "1s" and "0s" characterizing the data (e.g., the EMG data or status data) to be transmitted from the respective sensor device 104 to the TC 102, and will be reflected in the load modulations of the secondary carrier signal envelope on the secondary coil 108, and thus the induced amplitude modulations of the primary carrier signal envelope on the primary coil 106, as "lows" and "highs." The data on the modulation level control line 149b represents modulation index data generated by the controller/processor 128 in response to acquiring the command data acquired from the TC 102 by the downlink demodulator 138 for setting the modulation level of the respective sensor device 104. The modulation index data takes the form of a load modulation control word that is continually applied to the uplink modulator 140 via the modulation level control line 149b until the modulation index is changed in accordance with the command data acquired from the TC 102.

Thus, a binary "1" currently on the uplink data line 149a turns on the resistor banks 144 of the variable resistors 142a, 142b selected for modulation, resulting in a decrease in the positively polarized envelope and an increase in the negatively polarized envelope of the voltage across the secondary coil 104. As a result, the voltage envelope at the primary coil 104 is "low," indicating the particular bit value of "1." In contrast, a binary "0" currently on the uplink data line 149a turns off the resistor banks 144 of the variable resistors 142a, 142b selected for modulation, resulting in no change to the positively and negatively polarized envelopes of the voltage across the secondary coil 104. As a result, the voltage envelope at the primary coil 104 is "high," indicating the particular bit value of "0."

Figure 10:
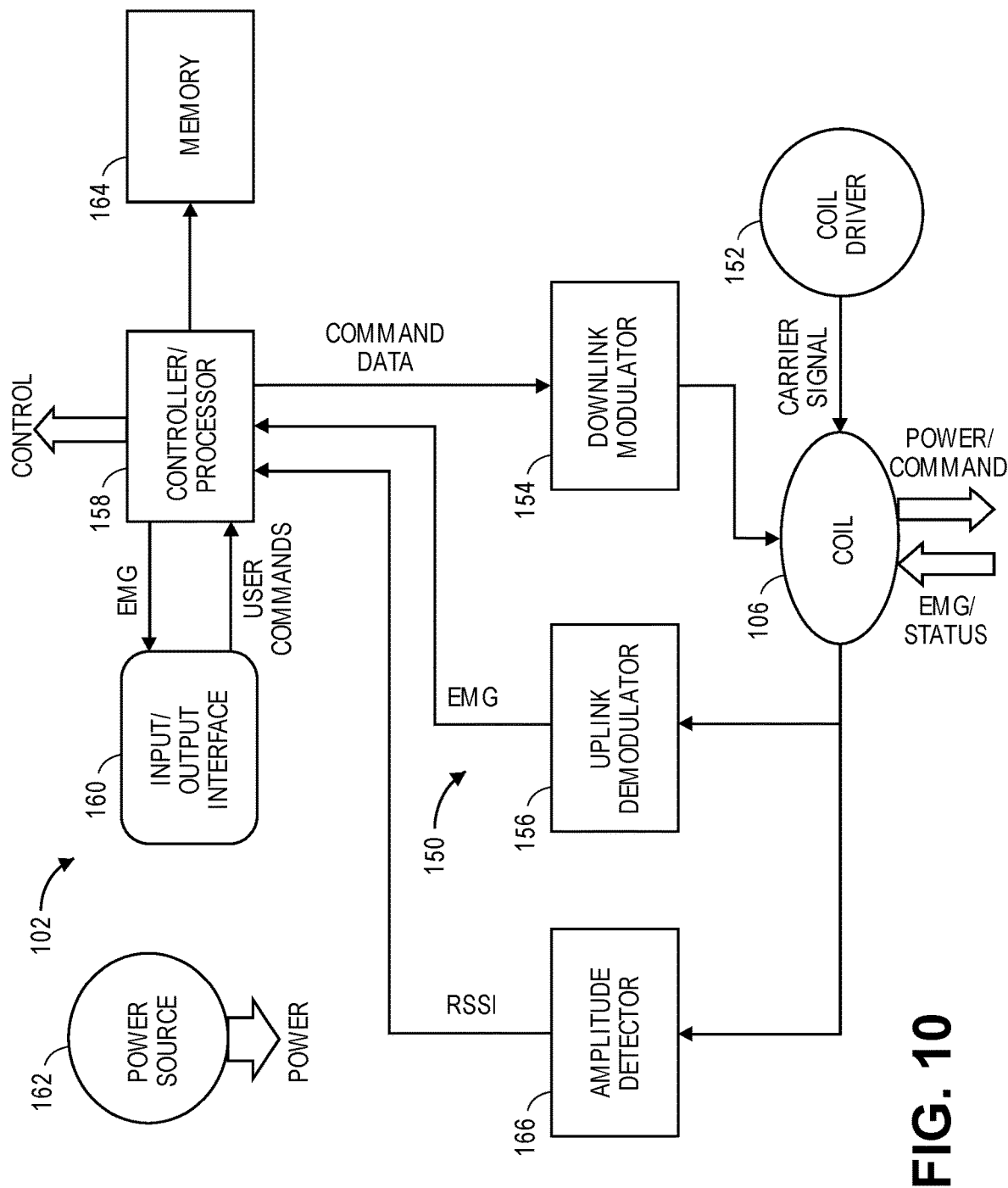
FIG. 10 is a block diagram of the telemetry controller illustrated in FIGS. 6a and 6b.

Referring to FIG. 10, the TC 102 comprises telemetry/power circuitry 150 configured for transmitting commands and power to the sensor devices 104 and receiving the EMG signal (either raw or filtered), or status signals, from the sensor devices 104. To this end, the telemetry/power circuitry 150 comprises the aforementioned primary coil 106 and a coil driver 152 configured for applying the primary carrier signal to the primary coil 106, thereby inducing the secondary carrier signals on the secondary coils 108 of the sensor devices 104.

As described above, the primary carrier signal is utilized as both a source of power and as a downlink/uplink carrier signal. To this end, the telemetry/power circuitry 150 further comprises a downlink modulator 154 configured for amplitude modulating the primary carrier signal envelope on the primary coil 106 at a pre-defined modulation level in accordance with the command data, thereby inducing an amplitude modulation of the secondary signal envelopes on the secondary coils 108 of the respective sensor devices 104, and allowing the sensor devices 104 to acquire the command data as described above. The telemetry/power circuitry 150 further comprises an uplink demodulator 156 configured for demodulating the primary carrier signal envelope on the primary coil 106 to acquire the EMG data (or status data) from the sensor devices 104.

The TC 102 further comprises a controller/processor 158 configured for controlling and operating the TC 102, and processing the EMG data (raw or filtered) received from the sensor device 104. The TC 102 further comprises an input/output interface 160, such as a USB port, for communicating the processed EMG data to, and receiving commands, from the prosthetic controller 110 via the cable 112 (shown in FIG. 4). The TC 102 further comprises a power source 162, e.g., a battery, for providing power to the circuitry of the TC 102, and memory 164 configured for storing information, such as EMG data.

Figure 11:
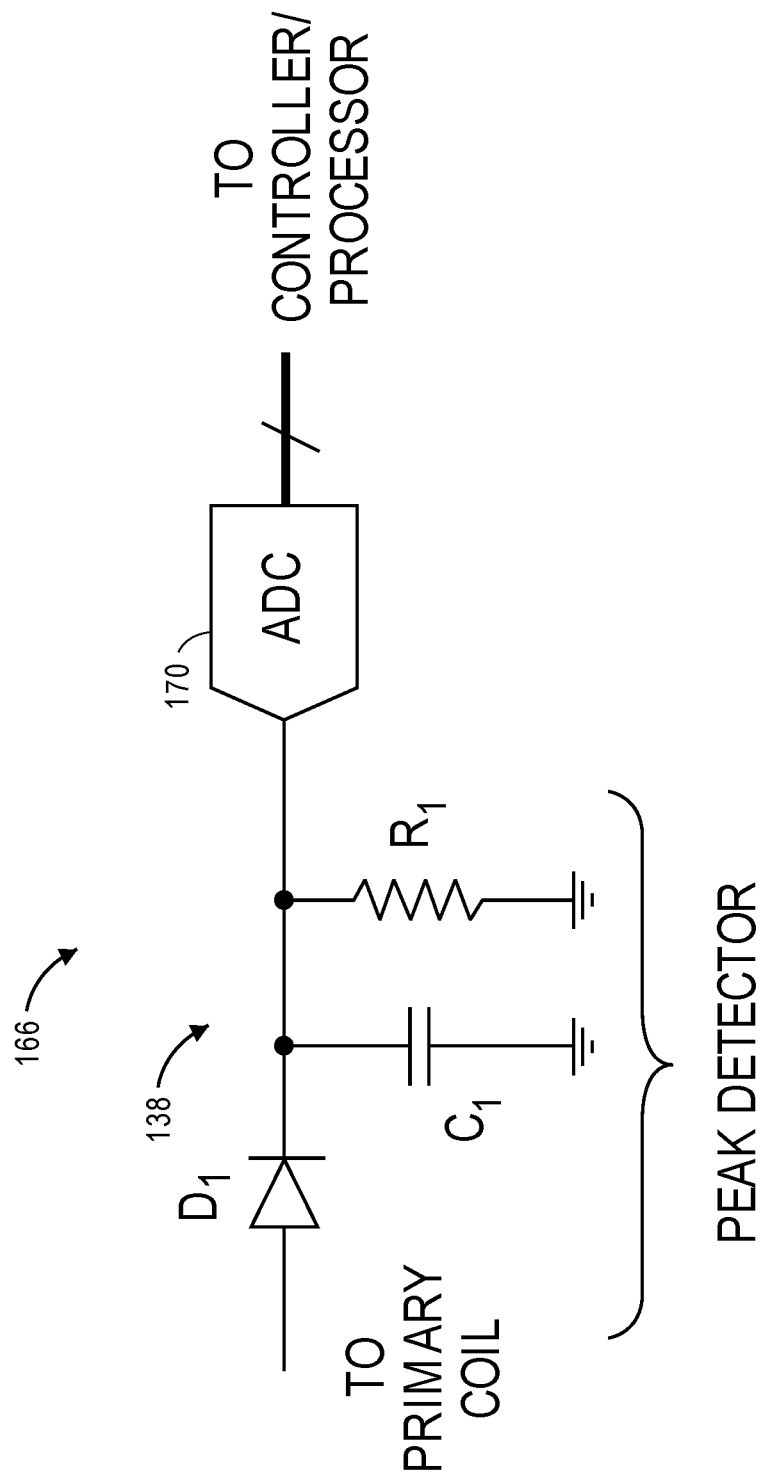
FIG. 11 is a schematic illustrating one embodiment of an amplitude detector used in the telemetry controller of FIG. 10.

The TC 102 further comprises an amplitude detector 166 configured for detecting the peak amplitude modulations induced on the primary carrier signal envelope of the primary coil 106 by the sensor devices 104. In one embodiment illustrated in FIG. 11, the amplitude detector 166 comprises a peak detector 168 comprising a diode D1 for sensing the positive envelope of the primary carrier signal on the primary coil 106, a capacitor C1 for sensing the local maxima of the positive envelope, and a resistor R1 for controlling the time for holding the maxima of the positive envelope. The amplitude detector 166 further comprises an analog-to-digital converter (ADC) 170 configured for digitizing the output of the peak detector 168.

Referring back to FIG. 10, the controller/processor 158 is configured for determining the RSSIs of the amplitude modulated primary carrier signal envelope induced on the primary coil 106 by the respective sensor devices 104 from the output of the peak detector 168, generates commands based on the determined RSSIs, and sends these commands via the telemetry/power circuitry 150 to the respective sensor device 104 to modify the modulation levels at which the sensor devices 104 load modulate the secondary carrier signal envelopes to equalizing modulation levels, as discussed above with respect to FIG. 7, thereby decreasing, and preferably minimizing, the variance between the RSSIs of the amplitude modulations of the primary carrier signal envelope induced on the primary coil 106 by the respective sensor devices 104. As will be described in further detail below, the controller/processor 158 may command the sensor devices 104 to iteratively command the sensor devices 104 to decrement the respective modulation levels and measure the RSSIs of the resulting amplitude modulations of the primary carrier signal envelope until the RSSIs are equalized, or alternatively, may approximate the modulation levels for the sensor devices 104 necessary to equalize the RSSIs, and command the sensor devices 104 to modify the respective modulation levels to these approximated modulation levels.

In this manner, the uplink demodulator 156 may acquire the EMG data from the primary carrier signal envelope in a conventional manner by first detecting the modulated primary carrier signal envelope, and then comparing the detected envelope of the primary carrier signal to a threshold level that is preferably centered between a minimum and a maximum of the modulated primary carrier signal envelope.

Figure 12A:
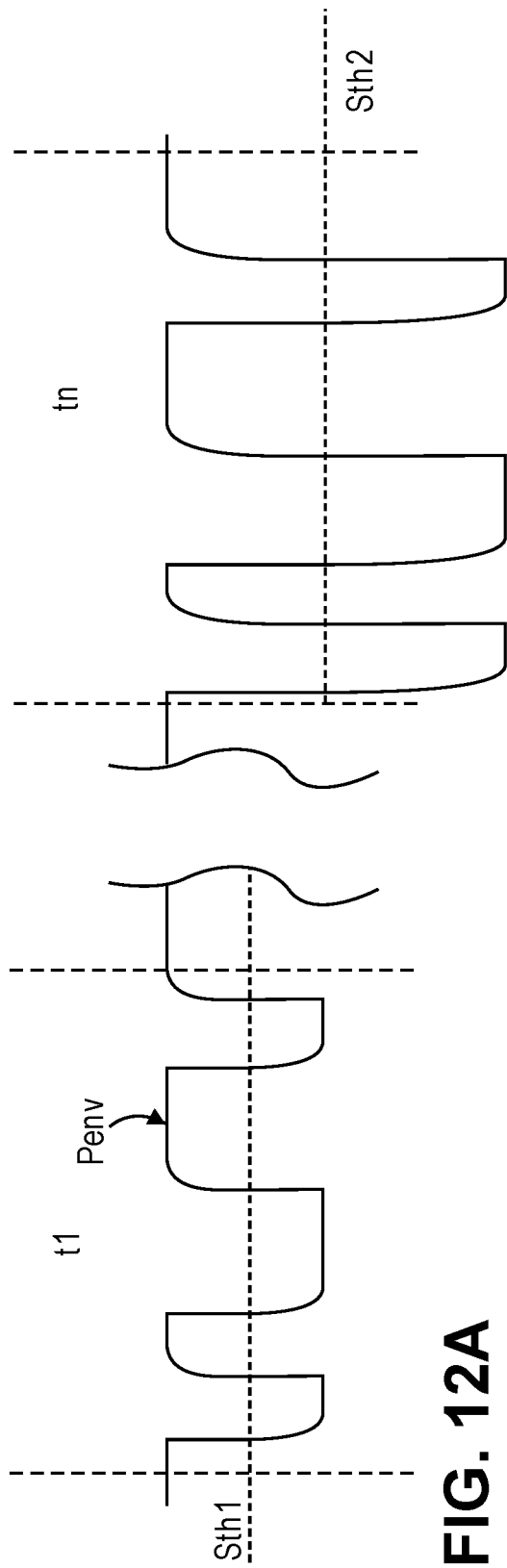
FIG. 12a is a diagram of a primary carrier signal on a primary coil of a prior art telemetry controller, particularly showing a non-uniform modulation of the primary carrier signal induced by the load modulation of secondary carrier signals on the secondary coils of sensor devices.
Figure 12B:
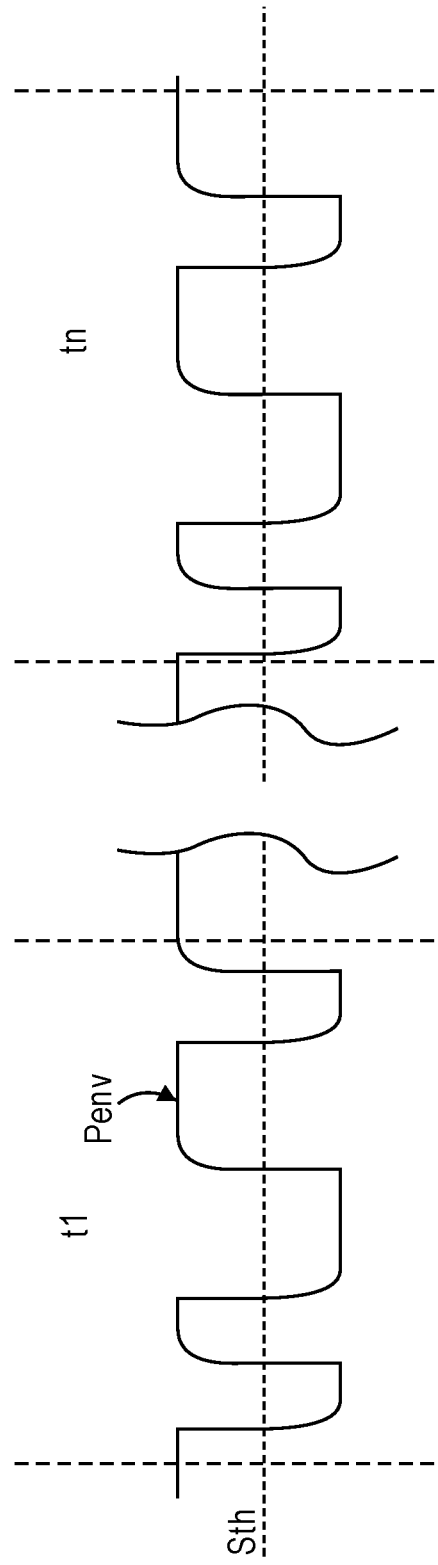
FIG. 12b is a diagram of a primary carrier signal on the primary coil of the telemetry controller of FIG. 11, particularly showing a uniform modulation of the primary carrier signal induced by the load modulation of secondary carrier signals on the secondary coils of the sensor devices of FIGS. 6a and 6b.

For example, as shown in FIGS. 12a and 12b, the data (e.g., EMG data) can be serially received from the sensor devices 104(1)-104(n) in an n number of dedicated time slots, respectively. As shown in FIG. 12a, without using the aforementioned compensation technique, the primary carrier signal envelope Penv is not uniformly modulated for the sensor devices 104 over time slots t1-tn, such that multiple threshold levels Sth1-Sthn must be used to acquire the data from the primary carrier signal envelope Penv. However, as shown in FIG. 12b, using the aforementioned compensation technique, the primary carrier signal envelope is substantially uniformly amplitude modulated for the sensors devices 104 over time slots t1-tn, such that a single threshold level Sth may be used. As the primary carrier signal envelope Penv crosses the threshold level Sth in one direction, a "1" or a "0" is detected (depending on the coding scheme), and as the primary carrier signal envelope Penv crosses the threshold level Sth in the other direction, a "0" or a "1" is detected. Thus, it can be appreciated that the demodulator 154 may utilize a simple comparator with a fixed threshold level to detect the uplink data. Although the primary carrier signal envelope Penv is described as being amplitude modulated in accordance with an amplitude shift keying (ASK) technique, it should be appreciated that the primary carrier signal envelope Penv may be amplitude modulated in accordance with other techniques, such as phase shift keying (PSK) and frequency shift keying (FSK) techniques.

With this in mind, the modulation levels of the respective sensor devices 104 can be adjusted, such that the RSSIs of the modulated signal envelopes Penv induced on the primary coil 108 by the sensor devices 104 during uplink communication is equalized across all of the sensor devices 104. As one example, one method 200 of equalizing the RSSIs of the implanted sensor devices 104 will be described with respect to FIG. 13. This method 200 can be performed one time, e.g., initially during startup (i.e., during initial communication between the sensor devices 104 and the TC 102 each time the prosthetic control system 100 is turned on) or may be performed periodically, e.g., monthly, weekly, daily, or even between data communication cycles.

First, communication links L are respectively established between the TC 102 and the sensor devices 104 (step 202). For example, the coil driver 152 of the TC 102 may apply a primary carrier signal having an envelope to the primary coil 106, thereby respectively inducing a secondary carrier signal having an envelope on each of the secondary coils 108 of the respective sensor device 104. In this case, the coupling coefficients Kc between the primary coil 108 of the TC 102 and the secondary coils 108 of the sensor devices 104 may substantially differ from each other, such that the RSSIs of the amplitude modulated communication links L by the sensor devices 104 will substantially differ from each other.

Next, the TC 102 commands all of the sensor devices 104 to respectively set the modulation levels to maximum modulation levels (step 204). For example, if the range of possible modulation levels is 1-35, the modulation levels may be set to 35. The TC 102 may broadcast a command to all of the sensor devices 104 or may individually send commands to the sensor devices 104, e.g., over the established communication links L, to set the modulation level to maximum. In the illustrated embodiment, the downlink modulator 154 of the TC 102 accomplishes this function by amplitude modulating the primary carrier signal envelope Penv on the primary coil 106 with the command(s), thereby inducing an amplitude modulation of the secondary carrier signal envelopes Senv, encoded with the command(s), on the secondary coils 108 of the sensor devices 104.

Next, all of the sensor devices 104 sequentially amplitude modulate the communication links L at the maximum modulation levels (step 206). For example, the uplink modulators 140 of the sensor devices 104 may sequentially load modulate the secondary carrier signals Senv on the secondary coils 108, thereby sequentially inducing amplitude modulations of the primary carrier signal envelope Penv on the primary coil 106 of the TC 102.

Next, the TC 102 respectively measures the RSSIs of the amplitude modulated communication links L for all of the sensor devices 104 (step 208). For example, the amplitude detector 166 of the TC 102 may detect the peak-to-peak values of the induced amplitude modulations of the primary carrier signal envelope Penv on the primary coil 106, and the controller/processor 158 may determine the RSSIs from these detected peak-to-peak values.

The variation of the RSSIs is then decreased by modifying, based on these determined RSSIs, at least one modulation level at which the respective communication link(s) L is amplitude modulated by the sensor devices 104 to obtain the equalizing modulation level(s).

In the illustrated embodiment, the controller/processor 158 of the TC 102 accomplishes this by first determining the lowest one of the RSSIs (step 210), and selecting one of the sensor devices 104 not associated with the lowest RSSI (step 212). For example, if it is determined that the first sensor device 104(1) is associated with the lowest RSSI, second sensor device 104(2) may be selected, although any sensor device 104 other than the sensor device 104(1), including the last sensor device 104(n), may be selected.

Next, the selected sensor device 104 modifies the respective modulation level to the equalizing modulation level, such that the RSSI of the amplitude modulated communication link L between the TC 102 and the selected sensor device 104 matches the lowest RSSI. It should be appreciated that, for the purposes of this specification, two or more RSSI's match each other if they are within a certain percentage of each other (preferably less than 50%, and more preferably less than 20%) or if they are as close to each other as possible given the granularity of the modulation levels.

The TC 102 accomplishes this function by commanding the selected sensor device 104 to modify the modulation level of the selected sensor device 104 to a new modulation level (step 214). In the illustrated embodiment, this function is accomplished by the controller/processor 158 of the TC 102, which generates the command, and the downlink modulator 154, which amplitude modulates the primary carrier signal envelope Penv on the primary coil 106 with the command, thereby inducing an amplitude modulation of the secondary carrier signal envelope Senv, encoded with the command, on the secondary coil 108 of the selected sensor device 104.

In one modulation level modification technique, the modulation level may be reduced by decrementing the modulation index by a predetermined amount, e.g., one, to the new modulation index. For example, if the modulation index is currently 35, the modulation index can be reduced to 34. In this case, the command sent by the TC 102 to the selected sensor device 104 will simply contain an instruction for the selected sensor device 104 to decrement the respective modulation index.

In another modulation level modification technique, instead of commanding the selected sensor device 104 to decrement the modulation index by a predetermined amount, the TC 102 may approximate a new modulation index of the selected sensor device 104 that will likely result in an RSSI that matches the lowest RSSI of the amplitude modulation of respective communication link L. That is, the TC 102 determines the difference between the RSSI associated with the selected sensor device 104 and the lowest RSSI, and approximates the change in the modulation index that would result in an RSSI that matches the lowest RSSI.

For example, if the difference between the RSSI of the communication link L associated with the selected sensor device 104 and the lowest RSSI is relatively large, the TC 102 may determine that a relatively large reduction in the modulation index associated with the selected sensor device 104 is required, and approximate based on this, a relatively large change in the modulation index that would result in an RSSI that matches the lowest RSSI. In contrast, if the difference between the RSSI of the communication link L associated with the selected sensor device 104 and the lowest RSSI is relatively small, the TC 102 may determine that a relatively large reduction in the modulation index associated with the selected sensor device 104 is required, and approximate based on this, a relatively small change in the modulation index that would result in an RSSI that matches the lowest RSSI.

The TC 102 then determines the new modulation index based on the approximate change in the modulation index (i.e., by subtracting the change from the previous modulation index), and commanding the selected sensor device 104 to change the modulation level in accordance with the new modulation index, e.g., by including the new modulation index within the command.

Regardless of the specific technique used, in response to commanding the selected sensor device 104 to modify the modulation level of the selected sensor device 104 to the new modulation level at step 214, the selected sensor device 104 amplitude modulates the respective communication link L at the new modulation level (step 216). In the illustrated embodiment, the selected sensor devices 104 accomplishes this function by load modulating the secondary carrier signal envelope Senv on the secondary coil 108, thereby inducing an amplitude modulation of the primary carrier signal envelope Penv on the primary coil 106 of the TC 102.

Next, the TC 102 measures the new RSSI of the newly amplitude modulated communication link L between the TC 102 and the selected sensor device 104 (step 218). For example, the amplitude detector 166 of the TC 102 may detect the peak-to-peak of the induced amplitude modulation of the primary carrier signal envelope Penv on the primary coil 106, and the controller/processor 158 may determine the RSSI from this detected peak-to-peak value. Then, the controller/processor 158 of the TC 102 compares the new RSSI to the lowest RSSI (step 220), and determines if there is a match between the new RSSI and the lowest RSSI (step 222).

If the new RSSI associated with the selected sensor device 104 does not match the lowest RSSI, the TC 102 repeats steps 214-222 until the RSSI of the amplitude modulated communication link L between the TC 102 and the selected sensor device 104 matches the lowest RSSI. In contrast, if the new RSSI associated with the selected sensor device 104 does match the lowest RSSI at step 222, the controller/processor 158 of the TC 102 then determines if all of the RSSIs of the amplitude modulated communication links L between the TC 102 and the sensor devices 104 match each other (step 224).

If the RSSI of the amplitude modulation communication link L between the TC 102 and at least one of the sensor devices 104 do match each other, the equalizing modulating level for that sensor device 104 will be achieved, and thus, the controller/processor 158 selects another sensor device 104 not associated with the lowest RSSI at step 212, and repeats steps 214-222 to modify the respective modulation level of the other selected sensor device 104 to another equalizing modulation level, such that the RSSI of the amplitude modulated communication link L between the TC 102 and the selected sensor device 104 matches the lowest RSSI.

If all of the RSSIs of the amplitude modulated communication links L between the TC 102 and the sensor devices 104 match each other at step 224, the RSSI equalization method 200 ends (step 226). However, given that the implanted sensor devices 104 may migrate or otherwise change in position at any subsequent time, thereby altering the RSSIs of the amplitude modulated communication links L between the TC 102 and the sensor devices 104, the RSSI equalization method 200 may be initialized during startup of the prosthetic control system 100 by starting at step 202, or if startup of the prosthetic control system 100 has already been performed, such that communication links L have been established between the TC 102 and the sensor devices 104, by starting at step 204.

Figure 14:
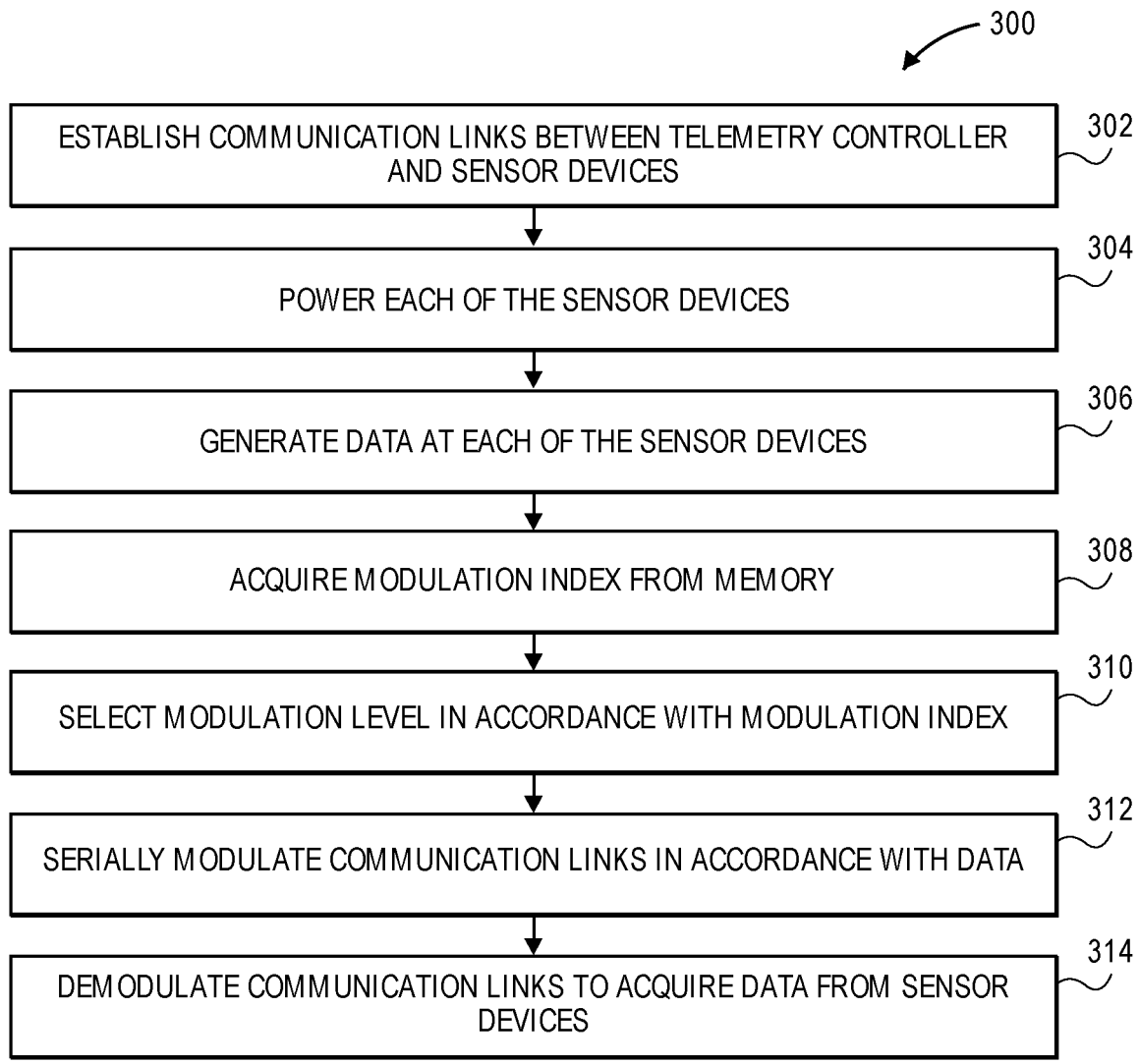
FIG. 14 is a flow diagram illustrating one method of communicating uplink data from the sensor devices to the telemetry controller of FIGS. 6a and 6b.

Once the RSSIs of the amplitude modulated communication links L between the TC 102 and the sensor devices 104 are equalized, the prosthetic control system 100 may then be operated in accordance with the method 300 illustrated in FIG. 14 to power the implanted sensor devices 104 and communicate physiological data, in this case, EMG data, of the patient 50 from the implanted sensor devices 104 to the TC 102 of the prosthetic control system 100.

Figure 13:
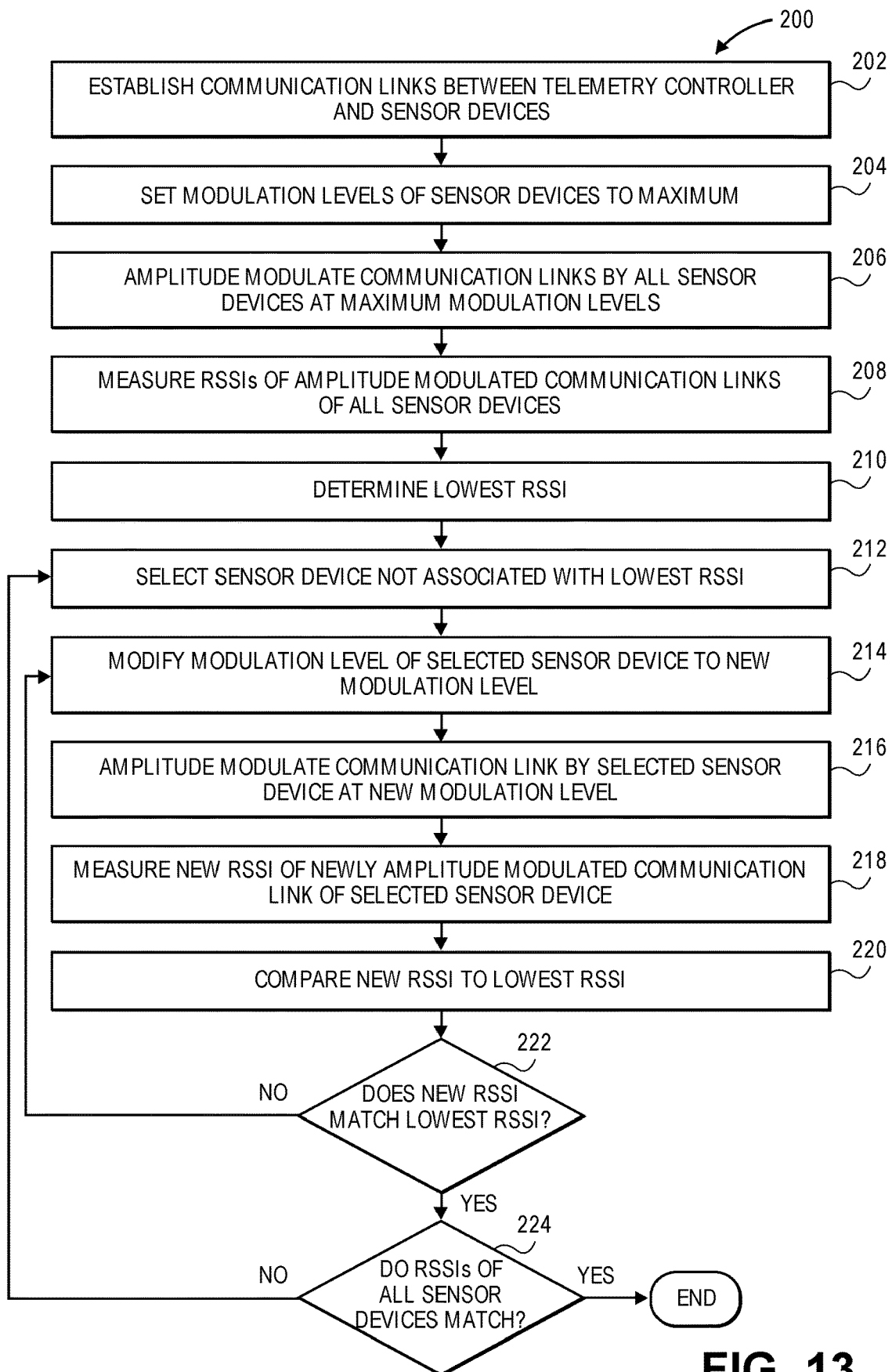
FIG. 13 is a flow diagram illustrating one method of equalizing the received signal strength indicator (RSSI) of communication links amplitude modulated by the sensor devices of FIGS. 6a and 6b.

The method 200 will be described with respect to FIG. 13. First, communication links L are respectively established between the TC 102 and the sensor devices 104 (step 302). For example, the coil driver 152 of the TC 102 may apply a primary carrier signal having an envelope to the primary coil 106, thereby respectively inducing a secondary carrier signal having an envelope on each of the secondary coils 108 of the respective sensor device 104. The rectifier 132 rectifies the respective secondary carrier signal, and the regulator 134 regulates and supplies the power to the circuitry of each of the sensor devices 104 (step 304). Next, each of the sensor devices 104 generates data, e.g., by acquiring EMG data from adjacent muscles of the patient 50 via the respective electrodes 120 (step 306).

Next, the controller/processor 128 of each of the sensor devices 104 acquires the respective modulation index from the memory 136 (step 308), and selects the modulation level of the respective uplink modulator 140 in accordance with the modulation index by outputting the modulation index on the modulation level control line 149b (step 310). Then, the uplink modulators 140 of the sensor devices 104 sequentially amplitude modulate the respective communication links L at the modulation levels in accordance with the data output on the uplink data line 149a by the respective controller/processor 128 (step 312). For example, the uplink demodulators 140 of the sensor devices 104 may load modulate the secondary carrier signals Senv on the secondary coils 108 at the modulation level in accordance with the data, thereby sequentially inducing amplitude modulations of the primary carrier signal envelope Penv on the primary coil 106 of the TC 102.

In this case, the coupling coefficients Kc between the primary coil 108 of the TC 102 and the secondary coils 108 of the sensor devices 104 may substantially differ from each other. However, because the modulation levels of the respective sensor devices 104 have been previously adjusted, the variance of the RSSIs of the amplitude modulated communication links L by the sensor devices 104 will be decreased, and preferably will be substantially uniform, e.g., less than 50%, and more preferably less than 20%.

Lastly, the uplink demodulator 156 of the TC 102 demodulates the modulated primary carrier signal envelope on the primary coil 106 to sequentially acquire the data from the sensor devices 104 (step 314). In the illustrated embodiment, the uplink demodulator 156 demodulates the modulated primary carrier signal by detecting the modulating primary carrier signal envelope, and comparing it to the threshold level centered between a minimum and a maximum of the modulated primary carrier signal envelope. The method 300 then returns to step 306 to generate and send data from the sensor devices 104 to the TC 102.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A medical system for use with a patient, comprising:
a plurality of implantable medical devices; and
a telemetry controller configured for establishing communication links between the implantable medical devices and the telemetry controller;
wherein the implantable medical devices are configured for amplitude modulating the communication links at modulation levels; and
wherein the telemetry controller is further configured for respectively measuring received signal strength indicators (RSSIs) of the amplitude modulated communication links, and decreasing a variation of the RSSIs by comparing the RSSIs to each other, determining the lowest one of the RSSIs, selecting one of the implantable medical devices not associated with the lowest RSSI, and commanding, based on the comparison of the measured RSSIs, the selected implantable medical device to modify a respective modulation level of the modulation levels at which a respective communication link is amplitude modulated by the selected implanted medical device to an equalizing modulation level, such that the RSSI of the respective communication link amplitude modulated at the modified respective modulation level by the selected implantable medical device matches the lowest RSSI.

2. The medical system of claim 1, wherein the telemetry controller is configured for commanding the selected implantable medical device to modify the respective modulation level to the equalizing modulation level by decrementing the respective modulation level by a predetermined amount at least one time.

3. The medical system of claim 1, wherein the telemetry controller is configured for commanding the selected implantable medical device to modify the respective modulation level to the equalizing modulation level by approximating a modulation level at which the RSSI of the respective communication link amplitude modulated at the approximated modulation level by the selected implantable medical device is likely to match the lowest RSSI.

4. The medical system of claim 1, wherein the telemetry controller is configured for commanding the selected implantable medical device to modify the respective modulation level to the equalizing modulation level by:
measuring the RSSI of the respective communication link amplitude modulated at the respective modified modulation level by the selected implantable medical device;
comparing the measured RSSI with the lowest RSSI; and
repeating the respective modulation level modifying, the RSSI measuring, and the measured RSSI comparison until the RSSI of the respective communication link amplitude modulated between the telemetry controller and the selected implantable medical device matches the lowest RSSI.

5. The medical system of claim 1, wherein the telemetry controller is further configured:
for selecting another one of the implantable medical devices not associated with the lowest RSSI; and
commanding the other selected implantable medical device to modify another respective modulation level to another equalizing modulation level, such that the RSSI of the respective communication link amplitude modulated at the other equalizing modulation level by the other selected implantable medical device matches the lowest RSSI.

6. The medical system of claim 5, wherein the telemetry controller is configured for repeating the selection of one of the implantable medical devices and the modification of the respective modulation level for all remaining ones of the implantable medical devices not associated with the lowest RSSI.

7. The medical system of claim 1,
wherein the implantable medical devices are configured for initially amplitude modulating the communication links at maximum modulation levels; and
wherein the telemetry controller is configured for commanding the selected implantable medical device to modify the respective modulation level to the equalizing modulation level by reducing a maximum modulation level of the maximum modulation levels at which the selected implantable medical device initially amplitude modulates the respective communication link to the respective equalizing modulation level.

8. The medical system of claim 1, wherein decreasing the variation between the RSSIs results in substantial uniformity between the RSSIs.

9. The medical system of claim 8, wherein the variation of the RSSIs is less than 50%.

10. The medical system of claim 8, wherein the variation of the RSSIs is less than 20%.

11. The medical system of claim 1,
wherein the implantable medical devices are further configured for respectively storing modulation indices that respectively set the modulation levels at which the implantable medical devices amplitude modulate the communication links; and
wherein the telemetry controller is further configured for commanding the selected implantable medical device to modify the respective modulation level by commanding the selected implantable medical device to modify a modulation index respectively of the modulation indices stored by the selected implantable medical device.

12. The medical system of claim 1,
wherein the implantable medical devices are further configured for generating data and sequentially amplitude modulating the communication links with the data by the implantable medical devices after the variation of the RSSIs has been decreased; and
wherein the telemetry controller is further configured for amplitude demodulating the communication links to acquire the data from the implantable medical devices.

13. The medical system of claim 12, wherein the data is physiological data acquired from the patient by the implantable medical devices.

14. The medical system of claim 12, wherein the data is operational status data of the implantable medical devices.

15. The medical system of claim 1,
wherein the telemetry controller comprises:
a primary coil; and
a coil driver configured for applying a primary carrier signal having an envelope to the primary coil; and
each of the implantable medical devices comprises:
a secondary coil on which a secondary carrier signal having an envelope may be induced in response to the application of the primary carrier signal on the primary coil, thereby establishing the respective communication link between the each implantable medical device and the telemetry controller; and
an uplink modulator configured for amplitude modulating the secondary carrier signal envelope at the respective modulation level, thereby inducing an amplitude modulation of the primary carrier signal envelope on the primary coil.

16. The medical system of claim 15,
wherein the telemetry controller further comprises:
an amplitude detector configured for detecting a peak-to-peak amplitude of the induced amplitude modulations of the primary carrier signal envelope;
control circuitry configured for determining the RSSIs from the detected peak-to-peak amplitudes, and generating a command based on the measured RSSIs; and
a downlink modulator configured for amplitude modulating the primary carrier signal envelope on the primary coil with the command, thereby inducing an amplitude modulation of the secondary carrier signal envelope, encoded with the respective command, on the secondary coil of the selected implantable medical device; and
the selected implantable medical device further comprises:
a downlink demodulator configured for amplitude demodulating the amplitude modulated secondary carrier signal envelope to acquire the command; and
control circuitry configured for modifying the respective modulation level in accordance with the command.

17. The medical system of claim 16, wherein the each of the implantable medical devices is configured for generating data, and the uplink modulator of the each implantable medical device is configured for amplitude modulating the secondary carrier signal envelope on the secondary coil with the data, such that the amplitude modulation of the primary carrier signal envelope induced on the primary coil of the telemetry controller is encoded with the data; and wherein the telemetry controller further comprises an uplink demodulator configured for amplitude demodulating the amplitude modulated primary carrier signal envelope to acquire the data.

18. The medical system of claim 17, wherein the uplink demodulator is configured for amplitude demodulating the amplitude modulated primary carrier signal envelope by:

detecting the amplitude modulated primary carrier signal envelope; and comparing the detected amplitude modulated primary carrier signal envelope to a threshold level amplitude.

19. The medical system of claim 18, wherein the amplitude of the threshold level is between a minimum and a maximum of the amplitude modulated primary carrier signal envelope.

20. The medical system of claim 19, wherein the amplitude of the threshold level is centered between the minimum and the maximum of the amplitude modulated primary carrier signal envelope.

21. The medical system of claim 15, wherein the each of the implantable medical devices further comprises a rectifier configured for rectifying and regulating the secondary carrier signal on the respective secondary coil for powering circuitry within the the implantable medical device.

22. The medical system of claim 15, wherein the uplink modulator of the each of the implantable medical devices is configured for load modulating the secondary carrier signal envelope on the respective secondary coil.

23. The medical system of claim 1, wherein the telemetry controller is an external telemetry controller.

24. A method of communicating between a telemetry controller and a plurality of medical devices implanted within a patient, comprising:

respectively establishing communication links between the telemetry controller and the implanted medical devices;

respectively amplitude modulating the communication links by the implanted medical devices at modulation levels;

respectively measuring received signal strength indicators (RSSIs) of the amplitude modulated communication links for the implanted medical devices; and decreasing a variation of the RSSIs by comparing the measured RSSIs, determining the lowest one of the RSSIs, selecting one of the implanted medical devices not associated with the lowest RSSI, and modifying, based on the comparison of the measured RSSIs, a respective modulation level of the modulation levels at which a respective communication link is amplitude modulated by the selected implanted medical device to an equalizing modulation level, such that the RSSI of the respective communication link amplitude modulated at the modified respective modulation level by the selected implantable medical device matches the lowest RSSI;

and commanding, based on the comparison of the RSSIs, the selected implantable medical device to modify a respective modulation level of the modulation levels at which a respective communication link is amplitude modulated to an equalizing modulation level, such that the RSSI of the respective communication link amplitude modulated at the modified respective modulation level by the selected implantable medical device matches the lowest RSSI.

25. The method of claim 24, wherein the modifying the respective modulation level to the equalizing modulation level comprises decrementing the respective modulation level by a predetermined amount at least one time.

26. The method of claim 24, wherein the modifying the respective modulation level to the respective equalizing modulation level comprises approximating a modulation level at which the RSSI of the respective communication link amplitude modulated at the approximated modulation level by the selected implantable medical device is likely to match the lowest RSSI.

27. The method of claim 24, wherein the modifying the respective modulation level to the equalizing modulation level comprises:

measuring the RSSI of the respective communication link amplitude modulated at the modified respective modulation level by the selected implantable medical device;

comparing the measured RSSI with the lowest RSSI; and repeating the respective modulation level modifying, the RSSI measuring, and the measured RSSI comparison steps until the RSSI of the respective communication link amplitude modulated communication between the telemetry controller and the selected implantable medical device matches the lowest RSSI.

28. The method of claim 24, further comprising:

selecting another one of the implanted medical devices not associated with the lowest RSSI; and modifying the respective modulation level to another equalizing modulation level, such that the RSSI of the respective communication link amplitude modulated at the other equalizing modulation level by the other selected implantable medical device matches the lowest RSSI.

29. The method of claim 28, further comprising repeating the selection of one of the implanted medical devices and the modification of the respective modulation level steps for all remaining ones of the implanted medical devices not associated with the lowest RSSI.

30. The method of claim 24, wherein the communication links are initially amplitude modulated by the implanted medical devices at maximum modulation levels; and wherein the respective first modulation level is modified to the respective equalizing modulation level by reducing a maximum modulation level of the maximum modulation levels at which the selected implantable medical device initially amplitude modulates the respective communication link to the respective equalizing modulation level.

31. The method of claim 24, wherein decreasing the variation between the RSSIs results in substantial uniformity between the RSSIs.

32. The method of claim 31, wherein the variation of the RSSIs is less than 50%.

33. The method of claim 31, wherein the variation of the RSSIs is less than 20%.

34. The method of claim 24, further comprising:

storing modulation indices in the implanted medical devices;

wherein the communication links are respectively amplitude modulated by the implanted medical devices in accordance with the modulation indices; and wherein the modifying the respective modulation level comprises modifying a modulation index of the modulation indices stored by the selected implanted medical device.

35. The method of claim 24, wherein the telemetry controller sends a command to the selected implanted medical device to modify the respective modulation level.

36. The method of claim 24, further comprising:
   generating data by the implanted medical devices;
   sequentially amplitude modulating the communication links with the data by the implanted medical devices after the variation of the RSSIs has been decreased; and
   amplitude demodulating the communication links by the telemetry controller to acquire the data from the implanted medical devices.

37. The method of claim 36, wherein the data is physiological data acquired from the patient by the implantable medical devices.

38. The method of claim 36, wherein the data is operational status data of the implantable medical devices.

39. The method of claim 24,
   wherein the telemetry controller has a primary coil and each of the medical devices has a secondary coil of a plurality of secondary coils;
   wherein the communication links between the implanted medical devices and the telemetry controller are established by applying a primary carrier signal having an envelope to the primary coil, thereby respectively inducing a secondary carrier signal having an envelope of a plurality of secondary carrier signal envelopes on each of the secondary coils; and
   wherein the communication links are amplitude modulated by the implanted medical devices by sequentially amplitude modulating each of the secondary carrier signal envelopes on the secondary coils, thereby inducing an amplitude modulation of the primary carrier signal envelope on the primary coil for the implanted medical devices.

40. The method of claim 39, wherein coupling coefficients between the primary coil and the secondary coils differ from each other.

41. The method of claim 39, wherein the telemetry controller sends a command to the selected implanted medical device to modify the respective modulation level by amplitude modulating the primary carrier signal envelope on the primary coil with the command, thereby inducing an amplitude modulation of the secondary carrier signal envelope, encoded with the command, on the secondary coil of the selected implanted medical device.

42. The method of claim 39, further comprising:
   generating data by the implanted medical devices;
   sequentially amplitude modulating the secondary carrier signal envelopes on the secondary coils with the data after the variation of the RSSIs has been decreased, thereby inducing the amplitude modulation of the primary carrier signal envelope, encoded with the data, on the primary coil for the implanted medical devices; and
   amplitude demodulating the amplitude modulated primary carrier signal envelope to acquire the data from the implanted medical devices.

43. The method of claim 42, wherein the amplitude demodulating the amplitude modulated primary carrier signal envelope comprises:
   detecting the amplitude modulated primary carrier signal envelope; and
   comparing the detected amplitude modulated primary carrier signal envelope to a threshold level amplitude.

44. The method of claim 43, wherein an amplitude of the threshold level is centered between a minimum and a maximum of the amplitude modulated primary carrier signal envelope.

45. The method of claim 39, further comprising generating power for the implanted medical devices from the respective secondary carrier signal envelopes.

46. The method of claim 39, wherein the amplitude modulating each of the secondary carrier signal envelopes comprises load modulating the each of the secondary carrier signal envelopes.

* * * * *